US012630621B2

(12) United States Patent
Tan

(10) Patent No.: US 12,630,621 B2
(45) Date of Patent: May 19, 2026

(54) HUMANIZED MONOCLONAL ANTIBODY AGAINST cANGPTL4

(71) Applicant: NANYANG TECHNOLOGICAL UNIVERSITY, Singapore (SG)

(72) Inventor: Nguan Soon Tan, Singapore (SG)

(73) Assignee: Nanyang Technological University, Singapore (SG)

( * ) Notice: Subject to any disclaimer, the term of this patent is extended or adjusted under 35 U.S.C. 154(b) by 739 days.

(21) Appl. No.: 17/997,165

(22) PCT Filed: Apr. 26, 2021

(86) PCT No.: PCT/SG2021/050230
§ 371 (c)(1),
(2) Date: Oct. 26, 2022

(87) PCT Pub. No.: WO2021/221565
PCT Pub. Date: Nov. 4, 2021

(65) Prior Publication Data
US 2023/0090156 A1     Mar. 23, 2023

(30) Foreign Application Priority Data

Apr. 27, 2020     (SG) ........................... 10202003838X

(51) Int. Cl.
| | |
|---|---|
| *C07K 16/22* | (2006.01) |
| *A61P 13/10* | (2006.01) |
| *A61P 35/00* | (2006.01) |
| A61K 39/00 | (2006.01) |

(52) U.S. Cl.
CPC .............. *C07K 16/22* (2013.01); *A61P 13/10* (2018.01); *A61P 35/00* (2018.01); *A61K 2039/505* (2013.01); *C07K 2317/24* (2013.01); *C07K 2317/92* (2013.01)

(58) Field of Classification Search
CPC ................ C07K 16/22; C07K 2317/24; C07K 2317/92; A61P 13/10; A61P 35/00; A61K 2039/505
See application file for complete search history.

(56) References Cited

U.S. PATENT DOCUMENTS

| | | | |
|---|---|---|---|
| 4,946,778 | A | 8/1990 | Ladner et al. |
| 4,975,278 | A | 12/1990 | Senter et al. |
| 5,208,020 | A | 5/1993 | Chari et al. |
| 5,225,539 | A | 7/1993 | Winter |
| 5,693,762 | A | 12/1997 | Queen et al. |
| 7,117,096 | B2 | 10/2006 | Luo et al. |
| 2003/0050331 | A1 | 3/2003 | Ng et al. |

FOREIGN PATENT DOCUMENTS

| | | | |
|---|---|---|---|
| WO | WO 8101145 A1 | 4/1981 | |
| WO | WO 8807378 A1 | 10/1988 | |
| WO | WO 2014027959 A1 | 2/2014 | |

OTHER PUBLICATIONS

Altschul et al., "Basic local alignment search tool," J. Mol. Biol. 215: 403-410, May 15, 1990.
Altschul et al., "Gapped BLAST and PSI-BLAST: a new generation of protein database search programs," Nucleic Acids Research 25(17):3389-3402, Jul. 16, 1997.
Beigier-Bompadre et al., "The formyl peptide N-formyl-methionyl-leucyl-phenylalanine downregulates the expression of FcγRs in interferon-γ-activated monocytes/macrophages in vitro and in vivo," Scandinavian Journal of Immunology 57:221-228, 2003.
Bird et al., "Single-chain antigen-binding proteins," Science 242(4877):423-426, Oct. 21, 1988.
Stella et al., "Prodrugs: A Chemical Approach to Targeted Drug Delivery," in Borchardt et al., Directed Drug Delivery, Clifton, New Jersey, USA, 1985, pp. 247-267.
Carter, "Potent antibody therapeutics by design," Nature Reviews Immunology 6:343-357, Apr. 18, 2006.
Chenna et al., "Multiple sequence alignment with the Clustal series of programs," Nucleic Acids Research 31(13):3497-3500, Mar. 4, 2003.
Craik et al., "The future of peptide-based drugs," Chem Biol Drugs Des (81):136-147, 2013.
De Pascalis et al., "Grafting of "abbreviated" complementarity-determining regions containing specificity-determining residues essential for ligand contact to engineer a less immunogenic humanized monoclonal antibody," The Journal of Immunology 169:3076-3084, 2002.
Dimitrov, "Therapeutic Antibodies: Methods and Protocols," Methods in Molecular Biology, New York, New York, USA, 2009, pp. xvii-585.
Farid, "Process economics of industrial monoclonal antibody manufacture," Journal of Chromatography B 848:8-18, 2007.
George et al., "Diagnostic and Therapeutic Antibodies," Methods in Molecular Medicine, Totowa, New Jersey, USA, Humana Press Inc., pp. xiv-477, 2000.
Goh et al., "Angiopoietin-like 4 interacts with matrix proteins to modulate wound healing," The Journal of Biological Chemistry 285(43):32999-33009, Oct. 22, 2010.
Goh et al., "Angiopoietin-like 4 interacts with integrins β1 and β5 to modulate keratinocyte migration," The American Journal of Pathology 177(6):2791-2803, Dec. 6, 2010.
Holliger et al., "Engineered antibody fragments and the rise of single domains," Nature Biotechnology 23(9):1126-1136, Sep. 2005.
Hsu et al., "Antidrug antibodies in psoriasis: a systematic review," British Journal of Dermatology 170: 261-273.
Huang et al., "ANGPTL4 modulates vascular junction integrity by integrin signaling and disruption of intercellular VE-cadherin and claudin-5 clusters," Blood 118(14):3990-4002, Oct. 6, 2011.

(Continued)

*Primary Examiner* — Nelson B Moseley, II
*Assistant Examiner* — Josephine K Darpolor
(74) *Attorney, Agent, or Firm* — Seed IP Law Group LLP

(57) ABSTRACT

The invention relates to humanized antibodies directed against C-terminal Angiopoietin-like 4 protein (cANGPTL4) and uses thereof, such as their use in treating cancer and methods of cancer treatment.

11 Claims, 5 Drawing Sheets

Specification includes a Sequence Listing.

(56) References Cited

OTHER PUBLICATIONS

Huston et al., "Protein engineering of antibody binding sites: recovery of specific activity in an anti-digoxin single-chain Fv analogue produced in *Escherichia coli*," Proc. Natl. Acad. Sci. USA 85:5879-5883, Aug. 1988.

Landon et al., "Therapeutic Antibodies," Springer-Verlag London Limited, London, EC1A 7BE, UK, 1995, pp. xii-231.

Massey, "Catalytic antibodies catching on," Nature 328:457-458, Jul. 30, 1987.

Maynard et al., "Antibody engineering," Annu. Rev. Biomed. Eng 2:339-376, 2000.

Morea et al., "Antibody structure, prediction and redesign," Biophysical Chemistry 68:9-16, 1997.

Morea et al., "Antibody modeling: implications for engineering and design," Methods 20:267-279, 2000.

Notredame et al., "T-Coffee: a novel method for fast and accurate multiple sequence alignment," J. Mol. Biol. 302: 205-217, 2000.

Penichet et al., "Antibody-cytokine fusion proteins for the therapy of cancer," Journal of Immunological Methods 248:91-101, 2001.

Roguska et al., "Humanization of murine monoclonal antibodies through variable domain resurfacing," Pro. Natl. Acad. Sci, USA 91:969-973, Feb. 1994.

Scott et al., "Antibody therapy of cancer," Nature Reviews Cancer 12:278-287, 2012.

Shi et al., "The state of the art on treatment of crohn's disease," The Japanese Society of Gastroenterology 53:989-998, 2018.

Sievers et al., "Antibody-drug conjugates in cancer therapy," Annu. Rev. Med. 64:15-29, 2013.

Sodhi et al., "Angiopoietin-like 4 binds neuropilins and cooperates with VEGF to induce diabetic macular edema," The Journal of Clinical Investigation 129(11):4593-4608, Nov. 2019.

Tan et al., ""Superhumanized" antibodies: reduction of immunogenic potential by complementarity-determining region grafting with human germline sequences: application to an anti-CD28," The Journal of Immunology 169(2):1119-1125, Jul. 15, 2002.

Thrush et al., "Immunotoxins: an update," Annu. Rev. Immunol. 14:49-71, 1996.

Trail et al., "Monoclonal antibody drug conjugates in the treatment of cancer," Current Opinion in Immunology 11:584-588, 1999.

Ward et al., "Binding activities of repertoire of single immunoglobulin variable domains secreted from *Escherichia coli*," Nature 341: 544-546, Oct. 12, 1989.

Zhu et al., "Angiopoietin-like 4: a decade of research," Bioscience Reports 32(3):211-219, 2012.

Amino acid sequence comparison between ANGH1-4 and ANGK1-4 with mAb11F6C4

Heavy Chain

```
11F6C4    QITLKESGPGILKPSQTLSLTCSFSGFSLS          WIRQPSGKGLEWLA           60
ANGH2     QVTLKESGPVLVKPTETLTLTCTVSGFSLS          WIRQPPGKALEWLA           60
ANGH4     QITLKESGPTLVKPTQTLTLTCTFSGFSLS          WIRQPPGKALEWLA           60
ANGH1     QITLKESGPTLVKPTQTLTLTCTFSGFSLS          WIRQPPGKALEWLA           60
ANGH3     QVTLKESGPTLVKPTQTLTLTCTFSGFSLS          WIRQPPGKALEWLA           60
          *:******* ::**::**:***:.*************** **.*************
```

```
11F6C4          QLTISKDTSRNQVFLKITSVDTADTATYYCAR          WGQGTTLTVSS  119
ANGH2           RLTISKDTSKSQVVLTMTNMDPVDTATYYCAR          WGQGTLVTVSS  119
ANGH4           RLTITKDTSKNQVDLTMTFMDPWDTATYYCAH          WGQGTLVTVSS  119
ANGH1           RLTITKDTSKNQVVLTMTNMDPVDTATYYCAR          WGQGTLVTVSS  119
ANGH3           RLTISKDTSKNQVVLTMTNMDPVDTATYYCAR          WGQGTTVTVSS  119
          *******:***:****:.** *.:* :*    *******:************* :****
```

ANGH1: SEQ ID NO:7
ANGH2: SEQ ID NO:9
ANGH3: SEQ ID NO:11
ANGH4: SEQ ID NO:13
11F6C4 VH domain: SEQ ID NO:23

Light Chain

```
11F6C4    DIVLTQSPASLAVSLGQRATISC          WFQQKPGQPPKLLIY          60
ANGK3     DIVMTQSPLSLPVTPGEPASISC          WYLQKPGQSPRLLIY          60
ANGK2     EIVLTQSPATLSLSPGERATLSC          WYQQKPGQAPRLLIY          60
ANGK1     DIVMTQSPDSLAVSLGERATINC          WYQQKPGQPPKLLIY          60
ANGK4     DIQMTQSPSSLSASVGDRVTITC          WYQQKPGKAPNLLIY          60
          :* :**** :*   : *: .::.*************: ****: *.**********
```

```
11F6C4    GIPARFSGSGSGTDFTLNIHPVEEEDAATYYC          FGGGTTLEIK  111
ANGK3     GVPDRFSGSGSGTDFTLKISRVEAEDVGVYYC          FGQGTKLEIK  111
ANGK2     GIPARFSGSGSGTDFTLTISSLEPEDFAVYYC          FGQGTKLEIK  111
ANGK1     GVPDRFSGSGSGTDFTLTISSLQAEDVAVYYC          FGQGTKVEIK  111
ANGK4     GVPSRFSGSGSGTDFTLTISSLQPEDFATYYC          FGEGTKVEIK  111
          *.* *************.*   :: ** ..*** ********* **.:***
```

ANGK1: SEQ ID NO:8
ANGK2: SEQ ID NO:10
ANGK3: SEQ ID NO:12
ANGK4: SEQ ID NO:14
11F6C4 VL domain: SEQ ID NO:24

Figure 1

A
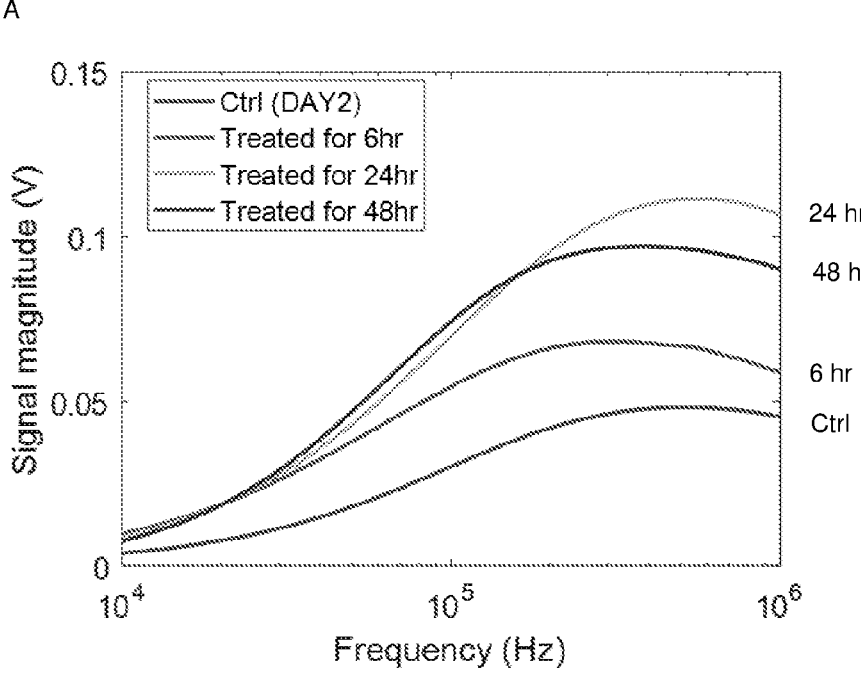
B
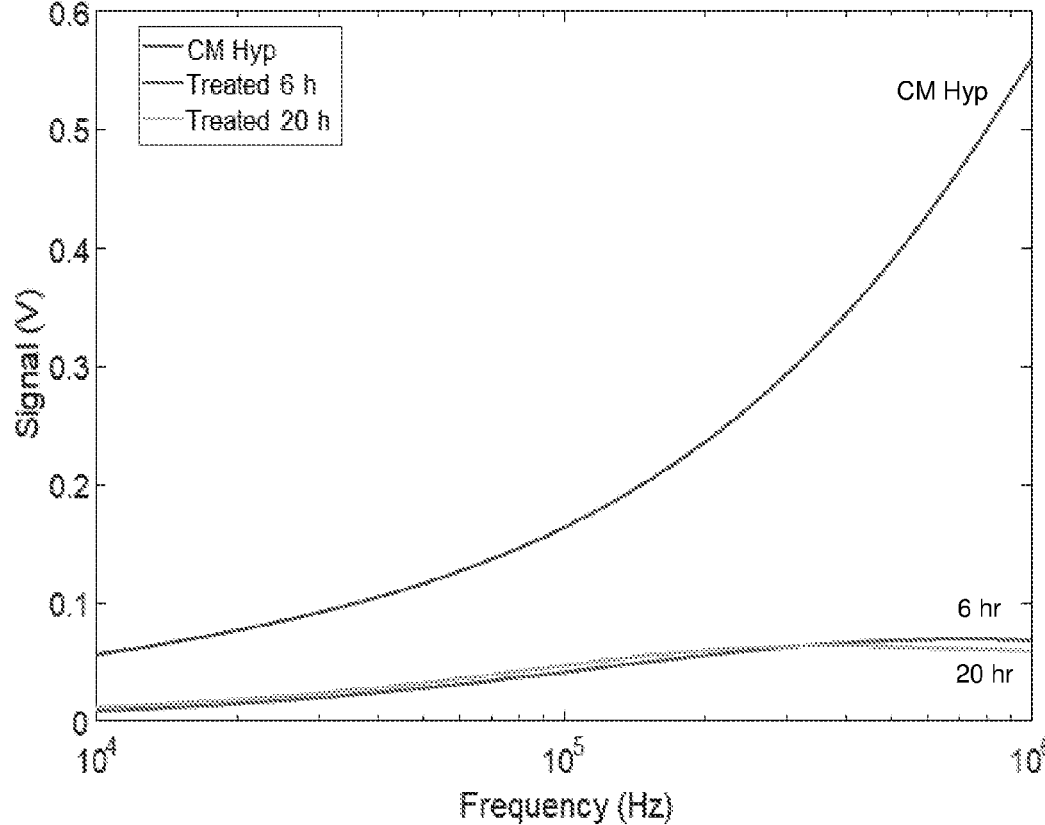
Figure 3

HUMANIZED MONOCLONAL ANTIBODY AGAINST cANGPTL4

REFERENCE TO AN ELECTRONIC SEQUENCE LISTING

The contents of the electronic sequence listing (SequenceListing690148602USPC.txt; Size: 17 kilobytes; and Date of Creation: Oct. 25, 2022) is herein incorporated by reference in its entirety.

CROSS-REFERENCE TO RELATED APPLICATION

This application claims the benefit of priority of Singapore Patent Application No. 10202003838X filed Apr. 27, 2020, the contents of which being hereby incorporated by reference in its entirety for all purposes.

FIELD OF THE INVENTION

The invention relates to humanized antibodies directed against the C-terminal part of Angiopoietin-like 4 protein (cANGPTL4) and uses thereof, such as their use in treating cancer and methods of cancer treatment.

BACKGROUND OF THE INVENTION

The ANGPTL proteins belong to a superfamily of angiogenic-regulating, secreted proteins that have high similarity to members of the angiopoietin family. ANGPTL4 is a member of the angiopoietin-like protein family and functions via a Tie2-independent mechanism (Zhu, P., et al., Angiopoietin-like 4: a decade of research. Biosci Rep, 2012. 32(3): p. 211-9). The full-length ANGPTL4 protein undergoes proteolytic processing to generate the N-terminal fragment (nANGPTL4) and the C-terminal fragment (cANGPTL4) in a tissue- and context-dependent manner. Through such post-translational modifications, ANGPTL4 has been shown to be involved in energy homeostasis, wound repair, tumorigenesis, angiogenesis, modulation of blood vessel permeability, and redox regulation. cANGPTL4 mediates its action via interaction with specific matrix proteins, integrins, claudins, cadherins and neuropilins (Sodhi, A., et al., Angiopoietin-like 4 binds neuropilins and cooperates with VEGF to induce diabetic macular edema. J Clin Invest, 2019. 129(11): p. 4593-4608; Huang, R. L., et al., ANGPTL4 modulates vascular junction integrity by integrin signaling and disruption of intercellular VE-cadherin and claudin-5 clusters. Blood, 2011. 118(14): p. 3990-4002; Goh, Y. Y., et al., Angiopoietin-like 4 interacts with integrins beta1 and beta5 to modulate keratinocyte migration. Am J Pathol, 2010. 177(6): p. 2791-803; Goh, Y. Y., et al., Angiopoietin-like 4 interacts with matrix proteins to modulate wound healing. J Biol Chem, 2010. 285(43): p. 32999-3009). mAbs that bind to cANGPTL4 and interfere with the interaction between cANGPTL4 and its various interacting partners can attenuate or abolished the function of cANGPTL4 in various diseases.

Murine antibodies directed against cANGPTL4 have been disclosed in international patent publication WO 2014/027959 A1.

Recent interest and advances in antibody therapies have provided the basis towards engineering antibodies as treatment and diagnosis of multiple human pathologies. The potential of antibodies in amelioration of diseases can be said to be beneficial, with fewer side effects than traditional chemotherapy or long-term drug usage, which can be advantageous for recovery time.

Currently, four types of monoclonal antibodies (mAbs) are available, murine, chimeric, humanized and human mAbs, each with their advantages and disadvantages. Murine mAbs are often generated via conventional hybridoma techniques, where the mouse is injected with specified antigen, fusion of isolated spleen cells with mutant myeloma line and subsequent selection for hybridomas secreting monoclonal antibodies into culture supernatant. For chimeric mAbs, the hybridomas are generated using the same technique as of murine monoclonal, but the genes coding for the murine antibody's variable region of heavy and light chains, and the constant region of the human heavy and light chains are inserted into a plasmid, which is then transfected into bacteria for subsequent production of chimeric antibodies as inclusion bodies.

However, murine and chimeric antibodies have the drawback of the complication of human anti-mouse antibody (HAMA) response. In humans, murine mAbs are often rejected by the host as the immune system deemed these mAbs as foreign, and consequently, chronic treatment with antibodies becomes ineffective due to mAbs having shorter half-life from undesired immune response, and side effects from immune complex formation. Even by replacing most of the non-antigen binding part with human antibody, like the chimeric mAbs, the HAMA response still persists, often causing similar side effects that are immunogenic in nature, although not as severe as that of murine mAbs.

To overcome said issues, humanized antibodies have been developed that allow for the minimization of HAMA response through complementarity-determining region (CDR) grafting. By grafting the six murine CDRs, together with human variable and constant regions gene into an expression vector and expressing them in mammalian cells humanized mAbs can be produced. This technique allows for antibodies with almost human antibody-like properties, which greatly reduces the immunogenic nature of the murine and chimeric mAbs, and consequently, prolonging the half-life of the humanized mAbs for chronic treatment, allowing for infrequent interventions instead.

The processes involved in CDR grafting require various design choices such as determining the boundaries of the CDRs, which human frameworks to use and which residues (if any) to substitute from the murine mAb into the human framework region. It has been found that the design is not straightforward and that success is not guaranteed, since binding strength and specificity of the parental antibody as well as antibody stability have to be retained while the undesired immunogenic properties in humans are to be reduced or removed. Furthermore, the recombinant production of the antibody in stable form needs to be achieved.

Even with the necessary steps to convert murine mAbs into humanized antibodies, caveats of humanized mAbs still have the potential to affect the therapeutic efficacy in later human clinical studies and subsequent treatment, or even cause severe side effects. One problem may arise from insufficient transferring of the CDR loops, which can affect the binding affinity retention compared to the original mAb construct, as the human framework of the variable and constant residues can affect the loops' orientations (George, A. J. T. and C. E. Urch, Diagnostic and therapeutic antibodies. Methods in molecular medicine. 2000, Totowa, N.J.: Humana Press. xiv, 477 p.) and may require further alterations and confirmation by testing in vivo to fully ascertain the specificity, affinity and downstream immunogenic side effects, if any, of the humanized mAbs.

These problems have hampered development so that to date no humanized blocking monoclonal antibodies against cANGPTL4 have been proposed.

SUMMARY OF THE INVENTION

The present invention meets this need and, in a first aspect of the invention, provides for a humanized antibody directed against the C-terminal region of angiopoietin-like 4 protein (cANGPTL4), said humanized antibody comprising a heavy chain variable domain and a light chain variable domain with human framework regions, the heavy chain variable domain comprising murine $V_H$ CDR1, $V_H$ CDR2, and $V_H$ CDR3 regions having the amino acid sequences set forth in SEQ ID Nos. 1-3, and the light chain variable domain comprising murine $V_L$ CDR1, $V_L$ CDR2, and $V_L$ CDR3 regions having the amino acid sequence set forth in SEQ ID Nos. 4-6, wherein:

(1) the heavy chain variable domain comprises or consists of the amino acid sequence set forth in SEQ ID NO:7 (ANGH1) or a variant thereof and the light chain variable domain comprises or consists of the amino acid sequence set forth in any one of SEQ ID Nos:8 (ANGK1), 10 (ANGK2), or 12 (ANGK3) or a variant thereof;

(2) the heavy chain variable domain comprises or consists of the amino acid sequence set forth in SEQ ID NO:9 (ANGH2) or a variant thereof and the light chain variable domain comprises or consists of the amino acid sequence set forth in any one of SEQ ID Nos:8 (ANGK1), 10 (ANGK2), or 12 (ANGK3) or a variant thereof;

(3) the heavy chain variable domain comprises or consists of the amino acid sequence set forth in SEQ ID NO:11 (ANGH3) or a variant thereof and the light chain variable domain comprises or consists of the amino acid sequence set forth in any one of SEQ ID Nos:8 (ANGK1), 10 (ANGK2), or 12 (ANGK3) or a variant thereof; or (4) the heavy chain variable domain comprises or consists of the amino acid sequence set forth in SEQ ID NO:13 (ANGH4) or a variant thereof and the light chain variable domain comprises or consists of the amino acid sequence set forth in SEQ ID NO:14 or a variant thereof, wherein the variants are invariable with respect to the CDR regions as defined in SEQ ID Nos. 1-6 and share at least 80% sequence identity with the respective reference sequence.

In various embodiments of the antibodies of the invention, (1) the heavy chain variable domain comprises or consists of the amino acid sequence set forth in SEQ ID NO:7 (ANGH1) or a variant thereof and the light chain variable domain comprises or consists of the amino acid sequence set forth in any one of SEQ ID Nos:8 (ANGK1), 10 (ANGK2), or 12 (ANGK3) or a variant thereof;

(2) the heavy chain variable domain comprises or consists of the amino acid sequence set forth in SEQ ID NO:9 (ANGH2) or a variant thereof and the light chain variable domain comprises or consists of the amino acid sequence set forth in any one of SEQ ID Nos:8 (ANGK1) or 12 (ANGK3) or a variant thereof;

(3) the heavy chain variable domain comprises or consists of the amino acid sequence set forth in SEQ ID NO:11 (ANGH3) or a variant thereof and the light chain variable domain comprises or consists of the amino acid sequence set forth in any one of SEQ ID Nos:10 (ANGK2) or 12 (ANGK3) or a variant thereof; or (4) the heavy chain variable domain comprises or consists of the amino acid sequence set forth in SEQ ID NO:13 (ANGH4) or a variant thereof and the light chain variable domain comprises or consists of the amino acid sequence set forth in SEQ ID NO:14 or a variant thereof.

In various embodiments of the antibodies of the invention, (1) the heavy chain variable domain comprises or consists of the amino acid sequence set forth in SEQ ID NO:7 or a variant thereof and the light chain variable domain comprises or consists of the amino acid sequence set forth in SEQ ID NO:8 or a variant thereof; or (2) the heavy chain variable domain comprises or consists of the amino acid sequence set forth in SEQ ID NO:11 or a variant thereof and the light chain variable domain comprises or consists of the amino acid sequence set forth in SEQ ID NO:12 or a variant thereof; or (3) the heavy chain variable domain comprises or consists of the amino acid sequence set forth in SEQ ID NO:13 or a variant thereof and the light chain variable domain comprises or consists of the amino acid sequence set forth in SEQ ID NO:14 or a variant thereof.

In one embodiment of the inventive antibodies, the heavy chain variable domain comprises or consists of the amino acid sequence set forth in SEQ ID NO:11 or a variant thereof and the light chain variable domain comprises or consists of the amino acid sequence set forth in SEQ ID NO:12 or a variant thereof.

In various embodiments, the variants of the light chain variable domain and heavy chain variable domain are invariable with respect to the CDR regions as defined above, i.e. any variation occurs in the framework region, and share, in various embodiments, at least 80%, preferably at least 81%, 82%, 83%, 84%, 85%, 86%, 87%, 88%, 89%, 90%, 91%, 92%, 93%, 94%, 95%, 96%, 97%, 98%, or 99% sequence identity with the respective reference sequence, i.e. any one of the amino acid sequences set forth in SEQ ID Nos. 7-14.

Another aspect of the invention relates to a method of treating a proliferative disease or disorder, preferably cancer, in a subject in need thereof, said method comprising administering a therapeutically effective amount of the antibody as described herein to said subject. Also encompassed are the antibodies disclosed herein for use as a pharmaceutical for the treatment or prevention of cancer.

Another aspect of the invention relates to an in vitro method of reducing cell proliferation, said method comprising contacting proliferating cells with an antibody as described herein.

A still further aspect of the invention relates to a nucleic acid molecule encoding a heavy and/or light chain of the antibody as disclosed herein. Also encompassed are recombinant host cells that comprise the nucleic acid of the invention.

Another aspect of the invention relates to a composition, preferably a pharmaceutical composition, comprising the antibody as described herein and a pharmaceutically acceptable carrier and/or excipient.

BRIEF DESCRIPTION OF THE DRAWINGS

In the following description, various embodiments of the invention are described with reference to the following drawings.

FIG. 1 shows an amino acid sequence alignment of the variable domains of the murine monoclonal antibody mAb11F6C4 and the variable domain sequences of the present invention. The shaded amino acid regions (dark letters) highlight the differences between the humanized and mouse-derived heavy and light chains. The CDR regions are shown as shaded boxes with white letters.

FIG. 3 shows (A) the secretion of ANGPTL4 from MIO-M1 after hypoxia treatment (verified with Western blot). Control medium was Normoxia medium from MIO-M1 cells after 48 h. Treatment medium was Hypoxia medium from MIO-M1 cells after 48 h. Measurements were taken at 6, 24 and 48 h; and (B) after addition of 10 ng of Antuzumab 1 to conditioned medium from hypoxia-treated MIO-M1 cells vascular leakiness caused by conditioned medium of hypoxia induced MIO-M1 was inhibited.

DETAILED DESCRIPTION OF THE INVENTION

Figure 2:
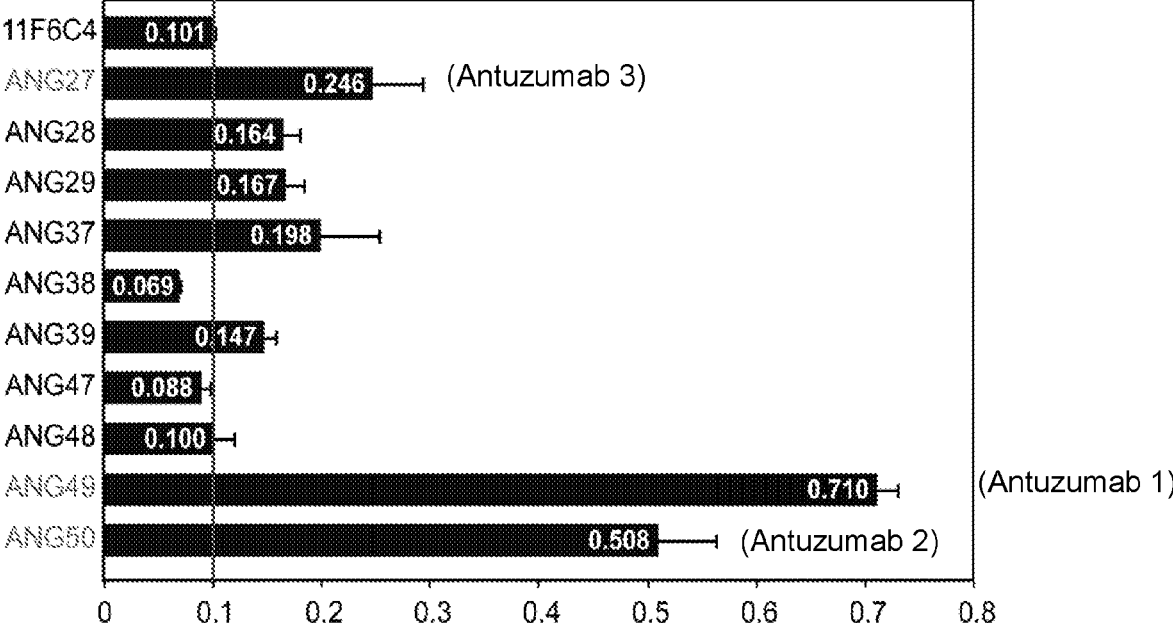
FIG. 2 shows the results of an ELISA assay of different humanized monoclonal antibodies against human cANGPTL4. The murine antibody mAb11F6C4 is used as a reference.

The inventors have previously shown in international patent publication WO 2014/027959 A1 that a murine monoclonal antibody against human cANGPTL4 (termed mAb11F6C4) showed reduced tumor vascular permeability and impaired tumor angiogenesis in mice and resulted in attenuated lung metastasis. Furthermore, treatment with the antibody (mAb11F6C4) significantly retarded melanoma growth in a mouse model, reproducing RNAi effects. mAb11F6C4 was found to target an epitope that resides within the C-terminus of human ANGPTL4 (cANGPTL4), and that it does not affect the mitochondrial activities and glucose regulations of this protein.

Based on these earlier results, the inventors developed a humanized version of said murine antibody by transferring the murine CDR regions into specific human framework regions and surprisingly found that certain CDR/framework combinations, as claimed herein, were significantly more stable and effective than others. Generally, as already explained above, the design of humanized antibodies is not mere routine, since the transfer of the complete CDR regions into a suitable framework region at positions that retain maximal binding strength and specificity of the parental antibody and its stability and simultaneously reducing the undesired immunogenic properties in humans.

Accordingly, one aspect of the invention relates to a humanized antibody directed against the C-terminal region of angiopoietin-like 4 protein (cANGPTL4), said humanized antibody comprising a heavy chain variable domain and a light chain variable domain with human framework regions, the heavy chain variable domain comprising murine $V_H$ CDR1, $V_H$ CDR2, and $V_H$ CDR3 regions having the amino acid sequences set forth in SEQ ID Nos. 1-3, and the light chain variable domain comprising murine $V_L$ CDR1, $V_L$ CDR2, and $V_L$ CDR3 regions having the amino acid sequence set forth in SEQ ID Nos. 4-6, wherein:

(1) the heavy chain variable domain comprises or consists of the amino acid sequence set forth in SEQ ID NO:7 (ANGH1) or a variant thereof and the light chain variable domain comprises or consists of the amino acid sequence set forth in any one of SEQ ID Nos:8 (ANGK1), 10 (ANGK2), or 12 (ANGK3) or a variant thereof;

(2) the heavy chain variable domain comprises or consists of the amino acid sequence set forth in SEQ ID NO:9 (ANGH2) or a variant thereof and the light chain variable domain comprises or consists of the amino acid sequence set forth in any one of SEQ ID Nos:8 (ANGK1), 10 (ANGK2), or 12 (ANGK3) or a variant thereof;

(3) the heavy chain variable domain comprises or consists of the amino acid sequence set forth in SEQ ID NO:11 (ANGH3) or a variant thereof and the light chain variable domain comprises or consists of the amino acid sequence set forth in any one of SEQ ID Nos:8 (ANGK1), 10 (ANGK2), or 12 (ANGK3) or a variant thereof; or (4) the heavy chain variable domain comprises or consists of the amino acid sequence set forth in SEQ ID NO:13 (ANGH4) or a variant thereof and the light chain variable domain comprises or consists of the amino acid sequence set forth in SEQ ID NO:14 or a variant thereof, wherein the variants are invariable with respect to the CDR regions as defined in SEQ ID Nos. 1-6 and share at least 80% sequence identity with the respective reference sequence.

The heavy chain variable region is also referred to herein as VH domain and the light chain variable region as VL domain.

The term "antibody", as used herein, refers to a protein consisting of one or more polypeptide chains substantially encoded by all or part of the known immunoglobulin genes. Known immunoglobulin genes, for example in humans, include the kappa (κ), lambda (λ), and heavy chain genetic loci, which together comprise the multitude of variable region genes, and the constant region genes mu (µ), delta (δ), gamma (γ), epsilon (ε), and alpha (α) which encode the IgM, IgD, IgG (IgG1, IgG2, IgG3, and IgG4), IgE, and IgA (IgA1 and IgA2) isotypes respectively. The term "antibody", as used herein is meant to include full length antibodies and antibody fragments, and may refer to a natural antibody from any organism, an engineered antibody, or an antibody generated recombinantly for experimental, therapeutic, or other purposes. The antibody fragments or variants referred to herein do however always include the heavy chain and light chain variable regions as disclosed herein. Accordingly, such fragments and variants include the known scFv fragments or scFv antibodies.

The terms "antibody" and "immunoglobulin" are used interchangeably herein to relate to polypeptides encoded by immunoglobulin genes. By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3.

In various embodiments the antibody of the invention is an IgG antibody, for example an IgG1 antibody or an IgG1 kappa antibody. Such an antibody typically comprises two identical heavy chains and two identical light chains, both having the Ig domains detailed below.

By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are VH, Cγ1, Cγ2, Cγ3, VL, and CL. As detailed above, VH and VL refer to the variable regions of the heavy ($V_H$) and light (VL) chain and are herein defined by reference to their amino acid sequence. Cγ1, Cγ2, and Cγ3 refer to the Ig domains of the constant part of the heavy chain, i.e. the domains more generally referred to as CH1, CH2 and CH3. The N-terminus of the CH1 or Cγ1 domain is linked to the C-terminus of the VH domain. CL relates to the constant part of the light chain and is linked to the C-terminus of the VL domain. The linkage is typically by a peptide bond. The full light chain thus comprises in N- to C-terminal orientation a VL and a CL domain. The full heavy chain thus comprises in N- to C-terminal orientation a VH, CH1, CH2 and CH3 domain. An IgG antibody comprises two full light chains and two full heavy chains.

The variable region of an antibody contains the antigen binding determinants of the molecule, and thus determines the specificity of an antibody for its target antigen The variable region is so named because it is the most distinct in sequence from other antibodies within the same class In the variable region, three loops are gathered for each of the variable (V) domains of the heavy chain and light chain to form an antigen-binding site Each of the loops is referred to as a complementarity-determining region (hereinafter referred to as a "CDR"), in which the variation in the amino acid sequence is most significant and which typically accounts for the binding specificity and affinity of the antibody. There are 6 CDRs total, three each per heavy and light chain, designated VH CDR1, VH CDR2, $V_H$ CDR3, $V_L$ CDR1, $V_L$ CDR2, and $V_L$ CDR3. The region of the variable domain outside of the CDRs is referred to as the framework region (FR). Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, and the conserved features of antibodies are disclosed, for example, in Maynard et al., 2000, Annu Rev Biomed Eng 2:339-376.

By "variable region" as used herein is meant the region of an immunoglobulin that comprises one or more Ig domains substantially encoded by any of the VL (Vκ, Vλ) and/or VH genes that make up the kappa, lambda, and heavy chain immunoglobulin genetic loci respectively.

By "constant region" of an antibody as defined herein is meant the region of the antibody that is encoded by one of the light or heavy chain immunoglobulin constant region genes.

By "constant light chain" or "light chain constant region" as used herein is meant the region of an antibody encoded by the kappa ($C_κ$) or lambda ($C_λ$) light chains. The constant light chain typically comprises a single domain, and as defined herein refers to positions 108-214 of $C_κ$ or lambda $C_λ$, wherein numbering is according to the EU index. An IgG1 kappa antibody thus comprises the kappa light chain constant region.

By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively For full length IgG antibodies, the constant heavy chain, as defined herein, refers to the N-terminus of the CH1 domain to the C-terminus of the CH3 domain, thus comprising positions 118-447, wherein numbering is according to the EU index.

The term "humanized", as used herein in relation to an antibody, generally refers to an antibody comprising a human framework region (FR) and one or more complementarity determining regions (CDRs) from a non-human (usually mouse or rat) antibody. The non-human antibody providing the CDRs is called the "donor" and the human immunoglobulin providing the framework is called the "acceptor". Humanization relies principally on the grafting of donor CDRs onto acceptor (human) $V_L$ and $V_H$ frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,693,762). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al. (1994, Proc Natl Acad Sci USA 91 969-973). In one embodiment, selection-based methods may be employed to humanize and/or affinity mature antibody variable regions, that is, to increase the affinity of the variable region for its target antigen. Other humanization methods may involve the grafting of only parts of the CDRs, including but not limited to methods described in, Tan et al, 2002, J Immunol 169 1119-1125, De Pascalis et al, 2002, J Immunol 169 3076-3084. Structure-based methods may be employed for humanization and affinity maturation, for example as described in U.S. Pat. No. 7,117,096 and related applications. The antibodies of the present invention are humanized in that they comprise a human FR and all 6 CDRs from the murine antibody mAb11F6C4 as described in international patent publication WO 2014/027959 A1.

In various embodiments, the antibody of the invention comprises a heavy chain and a light chain. In specific embodiments thereof, they comprise a human IgG1 constant region within a heavy chain of the immunoglobulin and a human constant region within a light chain of the immunoglobulin. The immunoglobulin comprises a human framework region within the variable domain of said heavy chain and within the variable domain of said light chain as defined by the amino acid sequences set forth herein. The remaining parts of the antibody, namely the constant regions of the heavy and light chain can be selected by those skilled in the art based on their common general knowledge.

The antibodies of the invention are directed against the C-terminal region of angiopoietin-like 4 protein (cANGPTL4). In various embodiments, this means that they specifically recognize and bind cANGPTL4. "Specifically binding" and "specific binding", as used herein, mean that an antibody binds to its target, i.e. human cANGPTL4, based on recognition of an epitope on the target molecule. The antibody recognizes and binds to the target molecule human cANGPTL4 with a binding affinity that is higher than that for other compounds that may be present. In various embodiments of the invention, "specifically binding" may mean that the antibody binds to the target molecule cANGPTL4 with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule, such as albumins. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the antibody uniquely recognizes and binds to the target analyte. According to preferred embodiments of the present invention, the binding affinities of the humanized antibodies disclosed herein are at least equal to those of the murine antibody mAb11F604, as described in WO 2014/027959 A1, preferably tested according to the protocols described in the Examples section of the present application.

The antibodies of the invention comprise a heavy chain and a light chain variable region, the heavy chain variable region comprising a $V_H$ CDR1, a $V_H$ CDR2, and a $V_H$ CDR3 region, and the light chain variable region comprising a $V_L$ CDR1, a $V_L$ CDR2, and a $V_L$ CDR3, wherein said $V_H$ CDR1 comprises, consists essentially of or consists of the amino acid sequence set forth in SEQ ID NO:1; said $V_H$ CDR2 comprises, consists essentially of or consists of the amino acid sequences set forth in SEQ ID NO:2; and said $V_H$ CDR3 comprises, consists essentially of or consists of the amino acid sequence set forth in SEQ ID NO:3; and said $V_L$ CDR1 comprises, consists essentially of or consists of the amino acid sequence set forth in SEQ ID NO:4; said $V_L$ CDR2 comprises, consists essentially of or consists of the amino acid sequence set forth in SEQ ID NO:5; said $V_L$ CDR3 comprises, consists essentially of or consists of the amino acid sequence set forth in SEQ ID NO:6. $V_L$ CDR3 with the amino acid sequence set forth in SEQ ID NO:6 may, in various embodiments, further comprise a T residue on the C-terminal end of said sequence stretch, i.e. after the W residue.

As defined herein, the antibodies of the invention may also comprise variants of the amino acid sequences of the heavy and light chain variable domains as defined by the amino acid sequences set forth in SEQ ID Nos. 7-14. Said variants are invariable with respect to the CDR regions as defined above, i.e. any variation occurs in the framework region. Said variants, in various embodiments, share at least 80%, preferably at least 81%, 82%, 83%, 84%, 85%, 86%, 87%, 88%, 89%, 90%, 91%, 92%, 93%, 94%, 95%, 96%, 97%, 98%, or 99% sequence identity with the amino acid sequences set forth in SEQ ID Nos. 7-12. The variations, typically amino acid substitutions or deletions, occur in the framework region and not in the CDRs. Possible are for example short truncations on the C- or N-terminus of the variable domain, typically 1, 2, 3 or 4 amino acids in length and/or single amino acid substitutions. In various embodiments, in the variants of the heavy chain variable domain the positions corresponding to positions 2, 10, 11, 12, 15, 16, 19, 23, 24, 43, 46, 68, 72, 77, 78, 83, 84, 86, 87, 89, 90, 99, 114, and 115 in SEQ ID NO:7, i.e. using the positional numbering of SEQ ID NO:7, are invariable (in addition to the CDR regions). In various embodiments, in the variants of the light chain variable domain the positions corresponding to positions 1, 3, 4, 9, 10, 12, 13, 14, 15, 17, 18, 19, 20, 21, 22, 40, 46, 47, 49, 62, 64, 78, 80, 81, 82, 83, 84, 87, 88, 89, 104, 107, and 108 in SEQ ID NO:8, i.e. using the positional numbering of SEQ ID NO:8, are invariable (in addition to the CDR regions).

By "amino acid" and "amino acid identity" as used herein is meant one of the 20 naturally occurring amino acids or any non-natural analogues that may be present at a specific, defined position. Thus "amino acid" as used herein is both naturally occurring and synthetic amino acids. For example, homophenylalanine, citrulline and noreleucine are considered amino acids for the purposes of the invention. "Amino acid" also includes imino acid residues such as proline and hydroxyproline. The side chain may be in either the (R) or the (S) configuration. In preferred embodiments, the amino acids are in the (S) or L-configuration. If non-naturally occurring side chains are used, such non-amino acid substituents may be used, for example, to prevent or retard in vivo degradation. Amino acid identity can easily be determined using alignments and methods well established in the field. For example, determination of the sequence identity of nucleic acid or amino acid sequences can be done by a sequence alignment based on well-established and commonly used BLAST algorithms (See, e.g. Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, S.3389-3402). Such an alignment is based on aligning similar nucleotide or amino acid sequences stretches with each other. Another algorithm known in the art for said purpose is the FASTA algorithm. Alignments, in particular multiple sequence comparisons, are typically done by using computer programs. Commonly used are the Clustal series (See, e.g., Chenna et al. (2003): Multiple sequence alignment with the Clustal series of programs. Nucleic Acid Research 31, 3497-3500), T-Coffee (See, e.g., Notredame et al. (2000): T-Coffee: A novel method for multiple sequence alignments. J. Mol. Biol. 302, 205-217) or programs based on these known programs or algorithms. Also possible are sequence alignments using the computer program Vector NTI® Suite 10.3 (Invitrogen Corporation, 1600 Faraday Avenue, Carlsbad, CA, USA) with the set standard parameters, with the AlignX module for sequence comparisons being based on the ClustalW. If not indicated otherwise, the sequence identity is determined using the BLAST algorithm. Such a comparison allows determination of the similarity of the compared sequences. Said similarity is typically expressed in percent identify, i.e. the portion of identical nucleotides/amino acids at the same or corresponding (in an alignment) sequence positions relative to the total number of the aligned nucleotides/amino acids. For example, if in an alignment 90 amino acids of a 100 aa long query sequence are identical to the amino acids in corresponding positions of a template sequence, the sequence identity is 90%. If not indicated otherwise, the "sequence identity" relates to the entire length of the aligned sequence.

In various embodiments of the antibodies of the invention, (1) the heavy chain variable domain comprises or consists of the amino acid sequence set forth in SEQ ID NO:7 (ANGH1) or a variant thereof and the light chain variable domain comprises or consists of the amino acid sequence set forth in any one of SEQ ID Nos:8 (ANGK1), 10 (ANGK2), or 12 (ANGK3) or a variant thereof;

(2) the heavy chain variable domain comprises or consists of the amino acid sequence set forth in SEQ ID NO:9 (ANGH2) or a variant thereof and the light chain variable domain comprises or consists of the amino acid sequence set forth in any one of SEQ ID Nos:8 (ANGK1) or 12 (ANGK3) or a variant thereof;

(3) the heavy chain variable domain comprises or consists of the amino acid sequence set forth in SEQ ID NO:11 (ANGH3) or a variant thereof and the light chain variable domain comprises or consists of the amino acid sequence set forth in any one of SEQ ID Nos:10 (ANGK2) or 12 (ANGK3) or a variant thereof; or (4) the heavy chain variable domain comprises or consists of the amino acid sequence set forth in SEQ ID NO:13 (ANGH4) or a variant thereof and the light chain variable domain comprises or consists of the amino acid sequence set forth in SEQ ID NO:14 or a variant thereof.

In various embodiments of the antibodies of the invention, the heavy chain variable domain comprises or consists of the amino acid sequence set forth in SEQ ID NO:7 and the light chain variable domain comprises or consists of the amino acid sequence set forth in SEQ ID NO:8.

In various other embodiments, the heavy chain variable domain comprises or consists of the amino acid sequence set forth in SEQ ID NO:11 and the light chain variable domain comprises or consists of the amino acid sequence set forth in SEQ ID NO:12.

In various embodiments, the heavy chain variable domain comprises or consists of the amino acid sequence set forth in SEQ ID NO:13 and the light chain variable domain comprises or consists of the amino acid sequence set forth in SEQ ID NO:14.

In the above embodiments, "comprises" means that the heavy and/or light chain variable domain can comprise additional amino acids on their C- or N-terminus. Typically, these extensions are however only 1-10 amino acids in length, for example 1, 2, 3, 4, 6, 7 or 8 amino acids in length.

In various embodiments, the above heavy chain variable domains consist of the indicated amino acid sequence, i.e. do not comprise any C- or N-terminal extensions. In various embodiments, this similarly or alternatively applies to the light chain variable domain.

The humanized antibodies of the invention are derived from a monoclonal antibody, more specifically the murine monoclonal antibody mAb11F6C4 as described in WO 2014/027959 A1.

Techniques described for the production of single chain antibodies (U.S. Pat. No. 4,946,778; Bird (1988), Science 242: 423-26; Huston, et al. (1988), Proc. Natl. Acad. Sci. USA, 85: 5879-83; and Ward, et al. (1989), Nature, 334: 544-46) can be adapted to produce gene-single chain antibodies comprising the heavy chain variable domain and the light chain variable domain of the invention. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments that can be produced by pepsin digestion of the antibody molecule and the Fab fragments that can be generated by reducing the disulfide bridges of the $F(ab')_2$ fragments. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

Alternatively, the antibodies can be a variety of structures, including, but not limited to antibody fragments. Antibody fragments include but are not limited to bispecific antibodies, minibodies, domain antibodies, synthetic antibodies, antibody mimetics, chimeric antibodies, antibody fusions (sometimes referred to as "antibody conjugates"), and fragments of each, respectively. Specific antibody fragments include, but are not limited to, (i) the Fab fragment consisting of $V_L$, $V_H$, CL and CH1 domains, (ii) the Fv fragment consisting of the $V_L$ and $V_H$ domains of a single antibody, (iii) $F(ab')_2$ fragments, a bivalent fragment comprising two linked Fab fragments (iv) single chain Fv molecules (scFv), wherein a $V_H$ domain and a $V_L$ domain are linked by a peptide linker which allows the two domains to associate to form an antigen binding site, (v) bispecific single chain Fv dimers and (vi) "diabodies" or "triabodies", multivalent or multispecific fragments constructed by gene fusion. In all these antibody variants, the CDR regions as defined herein are invariable and at least one heavy chain variable region and at least one light chain variable region, as defined herein, are comprised.

The antibody fragments may be modified. For example, the molecules may be stabilized by the incorporation of disulfide bridges linking the $V_H$ and $V_L$ domains. Examples of antibody formats and architectures are described in Holliger & Hudson, 2006, Nature Biotechnology 23(9):1126-1136, and Carter 2006, Nature Reviews Immunology 6:343-357.

Antibodies of the invention may include multispecific antibodies, notably bispecific antibodies, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9): 1126-1136.

In various embodiments, the antibody of the invention is an antibody fragment. Of particular interest are antibodies that comprise Fc regions, Fc fusions, and the constant region of the heavy chain (CH1-hinge-CH2-CH3) Antibodies of the present invention may comprise Fc fragments An Fc fragment of the present invention may comprise from 1-90% of the Fc region, e.g, 10-90%, 30-90%, etc Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contain extra polypeptide sequence.

In one embodiment, the antibodies of the invention are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588. Possible conjugate partners include but are not limited to cytokines, cytotoxic agents, toxins, radioisotopes, chemotherapeutic agent, anti-angiogenic agents, a tyrosine kinase inhibitors, and other therapeutically active agents.

In various embodiments, conjugate partners may be considered payloads, that is to say that the goal of a conjugate is targeted delivery of the conjugate partner to a targeted cell, for example a cancer cell or immune cell, by the antibody. Thus, for example, the conjugation of a toxin to an antibody targets the delivery of the toxin to cells expressing the target antigen. As will be appreciated by one skilled in the art, in reality the concepts and definitions of fusion and conjugate are overlapping. The designation of an antibody as a fusion or conjugate is not meant to constrain it to any particular embodiment of the present invention. Rather, these terms are used loosely to convey the broad concept that any antibody of the present invention may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, aunstatins, geldanamycin, maytansine, and duocarmycins and analogs; for the latter, see U.S. patent application 2003/0050331.

In various embodiments, the antibodies of the present invention are fused or conjugated to a cytokine. By "cytokine" as used herein is meant a generic term for proteins released by one cell population that act on another cell as intercellular mediators. For example, as described in Penichet et al., 2001, J Immunol Methods 248-91-101, cytokines may be fused to antibody to provide an array of desirable properties Examples of such cytokines are lymphokines, monokines, and traditional polypeptide hormones. Included among the cytokines are growth hormone such as human growth hormone, N-methionyl human growth hormone, and bovine growth hormone; parathyroid hormone, thyroxine; insulin; proinsuhn; relaxin, prorelaxin; glycoprotein hormones such as follicle stimulating hormone (FSH), thyroid stimulating hormone (TSH), and luteinizing hormone (LH); hepatic growth factor; fibroblast growth factor, prolactin, placental lactogen; tumor necrosis factor-alpha and -beta; mulle[pi]an-inhibiting substance, mouse gonadotropin-associated peptide; inhibin; activin, vascular endothelial growth factor; integrin; thrombopoietin (TPO); nerve growth factors such as NGF-beta; platelet-growth factor, transforming growth factors (TGFs) such as TGF-alpha and TGF-beta; insulin-like growth factor-I and -II; erythropoietin (EPO); osteoinductive factors, interferons such as interferon-alpha, beta, and -gamma; colony stimulating factors (CSFs) such as macrophage-CSF (M-CSF), granulocyte-macrophage-CSF (GM-CSF); and granulocyte-CSF (G-CSF), interleukins (ILs) such as IL-1, IL-1alpha, IL-2, IL-3, IL-4, IL-5, IL-6, IL-7, IL-8, IL-9, IL-10, IL-11, IL-12, IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In other various embodiments, the antibodies of the present invention are fused, conjugated, or operably linked to a toxin, including but not limited to small molecule toxins and enzymatically active toxins of bacterial, fungal, plant or animal origin, including fragments and/or variants thereof For example, a variety of immunotoxins and immunotoxin methods are described in Thrush et al., 1996, Ann. Rev. Immunol. 14:49-71. Small molecule toxins include but are not limited to calicheamicin, maytansine (U.S. Pat. No. 5,208,020), trichothene, and CC1065. Dolastatin 10 analogs such as auristatin E (AE) and monomethylauristatin E (MMAE) may find use as conjugates for the antibodies of the present invention. Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, sapaonaria *officinalis* inhibitor, gelonin, mitogellin, restrictocin, phenomycin, enomycin and the tricothecenes. The present invention further contemplates a conjugate between an antibody of the present invention and a compound with nucleolytic activity, for example a ribonuclease or DNA endonuclease such as a deoxyribonuclease (DNase).

In still further various embodiments, an antibody of the present invention may be fused, conjugated, or operably linked to a radioisotope to form a radioconjugate. A variety of radioactive isotopes are available for the production of radioconjugate antibodies. Examples include, but are not limited to, At211, 1131, 1125, Y90, Re186, Re188, Sm153, Bi212, P32, and radioactive isotopes of Lu.

In various other embodiments, an antibody of the present invention may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT application WO 81/01145, incorporated herein it its entirety by reference) to an active anti-cancer drug. See, for example, PCT application WO 88/07378 or U.S. Pat. No. 4,975,278, each incorporated herein it its entirety by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents, carbohydrate-cleaving enzymes such as beta-galactosidase and neuramimidase useful for converting glycosylated prodrugs into free drugs, beta-lactamase useful for converting drugs derivatized with alpha-lactams into free drugs, and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert prodrugs into free active drugs (see, for example, Massey, 1987, Nature 328. 457-458, incorporated herein it its entirety by reference). Antibody-abzyme conjugates can be prepared for delivery of the abzyme to a tumor cell population. A variety of additional conjugates are contemplated for the antibodies of the present invention. A variety of chemotherapeutic agents, anti-angiogenic agents, tyrosine kinase inhibitors, and other therapeutic agents are described below, which may find use as antibody conjugates.

Preferably the antibody described herein is suitable for use in treatment of a proliferative disease, in particular a tumor. A tumor as defined here is a cancer or neoplasm that may include melanoma, prostate cancer, colon cancer, liver cancer, bladder cancer, breast cancer or lung cancer. Any one of the cancer cell lines where the expression of Angptl4 was found to be elevated is included in the term tumor or cancer. Any of the cancers from which these cancer cell lines were derived is also included in the term tumor or cancer. Metastatic cancer is included in the term tumor or cancer.

One aspect if the invention therefore relates to a method of treating a patient suffering from a proliferative disease or disorder, preferably cancer. Said method may comprise administering a therapeutically effective amount of the antibody as described herein to said subject. Also encompassed are the antibodies of the invention for use as a medicament, for example for use in a method of treating a proliferative disease or disorder, such as cancer or a tumor.

"Treatment" and "treat" and synonyms thereof refer to therapeutic treatment wherein the object is to stop or reduce cell proliferation in (cancerous) cells. Preferably, stopping or reducing cell proliferation will in turn stop or halt the growth of a tumor or reduce (decrease) the size of the tumor or stop or slow metastasis. Those in need of such treatment include an individual or patient that has been diagnosed with cancer, a neoplasm or metastatic cancer. A patient or an individual refers to an animal, such as a mammal, preferably a human. However, in various embodiments, the cell is in vitro and the method is an in vitro method. In various other embodiments, the cell is in vivo and the antibody is administered to a subject such as a patient or individual in need of treatment.

One aspect of the invention therefore also relates to an in vitro method of reducing cell proliferation, which comprises the step of contacting proliferating cells with an antibody as described herein. In various embodiments, the in vitro cell is a cell line. In various other the antibody may be administered to a cell for reducing cell proliferation in cancerous cells.

Preferably the antibody administered to a subject is in a therapeutically effective amount. A therapeutically effective amount would be able to block angiopoietin like 4 protein (ANGPTL4) polypeptide in a proliferating cell in culture or at a tumor site.

As used herein a "therapeutically effective amount" of the antibody will be an amount that is capable of stopping or halting cell proliferation that may result in stopping or halting growth of a tumor or reducing (decreasing) the size of the tumor. It may also refer to the prevention. Dosages and administration of an antibody of the invention in a pharmaceutical composition may be determined by one of ordinary skill in the art of clinical pharmacology or pharmacokinetics. An effective amount of the antibody to be employed therapeutically, for example an antibody as described herein, will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng to up to 100 mg more per day, preferably about 1 µg to 10 mg per day. Doses may include antibody amount anywhere in the range of 10 to 100 µg or more preferably 25, 50, or 75 µg per day.

Another aspect of the invention relates to a nucleic acid molecule encoding a heavy or light chain variable domain of the antibody described herein.

The terms "polynucleotide" and "nucleic acid (molecule)" are used interchangeably herein to refer to polymeric forms of nucleotides of any length, including naturally occurring and non-naturally occurring nucleic acids. The polynucleotides may contain deoxyribonucleotides, ribonucleotides and/or their analogs. Methods for selection and preparation of nucleic acids are diverse and well described in standard biomolecular protocols. A typical way would be preparative PCR and chromatographic purification starting from existing template DNAs or stepwise synthesis of artificial nucleic acids. Typically, the nucleic acid molecules referred to herein are DNA molecules.

In various embodiments the nucleic acid molecule comprises a nucleotide sequence encoding the variable domain of the light chain set forth in SEQ ID Nos: 16, 18, 20 or 22.

Similarly, in various embodiments the nucleic acid molecule comprises a nucleotide sequence encoding the variable domain of the heavy chain set forth in SEQ ID Nos: 15, 17, 19, or 21.

The invention may further include an expression system comprising:
(i) a first gene encoding for a light chain variable region or the complete light chain; and
(ii) a second gene encoding for a heavy chain variable region or the complete heavy chain;
wherein the expression system is optionally inducible to express an antibody as described herein.

Preferably the expression systems are a cell-based expression systems either in prokaryotic or eukaryotic cells as described above.

Another aspect of the invention relates to a composition for treating cancer comprising the antibody as described herein and a carrier and/or excipient.

Formulations of the antibodies of the present invention may be prepared for storage by mixing the antibody having the desired degree of purity with optional pharmaceutically acceptable carriers, excipients or stabilizers (Remington's Pharmaceutical Sciences 16th edition, Osol, A. Ed., 1980), for example in the form of lyophilized formulations or aqueous solutions. Acceptable carriers, excipients, or stabilizers are pharmaceutically acceptable, i.e. nontoxic to recipients, at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or other immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG).

In one embodiment, the pharmaceutical composition that comprises the antibody of the present invention may be in a water-soluble form, such as comprising certain ingredients in form of pharmaceutically acceptable salts, such as acid and/or base addition salts. The formulations to be used for in vivo administration are typically sterile. This is readily accomplished by known methods.

The antibodies disclosed herein may also be formulated as immunoliposomes or in microcapsules. Techniques for preparing such formulations are disclosed in Remington's Pharmaceutical Sciences 16th edition, Osol, A. Ed., 1980.

Administration of the pharmaceutical composition comprising an antibody of the present invention, e.g., in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of administration.

Protein therapeutics are often delivered by IV infusion or bolus. The antibodies of the present invention may, in various embodiments, also be delivered using such methods. For example, administration may be by intravenous infusion with 0.9% sodium chloride as an infusion vehicle or carrier.

The amounts and frequencies of administration are, in various embodiments, selected to be therapeutically or prophylactically effective. As is known in the art, adjustments for protein degradation, systemic versus localized delivery, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In one embodiment, the concentration of the antibody is in the range of 0.003 μM to 1.0 M.

In order to treat a patient, a therapeutically effective dose of the antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, e.g., 1 to 10 mg/kg of body weight.

In some embodiments, only a single dose of the antibody is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

The antibodies of the present invention may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody of the present invention may be administered to the patient along with chemotherapy, radiation therapy, or both chemotherapy and radiation therapy. The antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of the prophylactic or therapeutic agents at exactly the same time. Instead, it is meant that the antibody of the present invention and the other agent or agents are administered in a sequence and within a time interval such that they may act together to provide a benefit that is increased versus treatment with only either the antibody of the present invention or the other agent or agents. In one embodiment, that the antibody and the other agent or agents act additively, in another embodiment they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In various embodiments, such co-administration also requires co-formulation of the active agents in one pharmaceutical composition, as defined herein.

In various embodiments, the antibodies of the present invention are administered in combination with one or more additional molecules, such as other antibodies or Fc molecules. The antibodies of the present invention may be co-administered with one or more other antibodies that have efficacy in treating the same disease or an additional comorbidity, for example two antibodies may be administered that recognize two antigens that are overexpressed in a given type of cancer.

In various embodiments, the antibodies of the present invention are co-administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide; alkyl sulfonates such as busulfan, improsulfan and piposulfan, androgens such as calusterone, dromostanolone propionate, epitiostanol, mepitiostane, testolactone, anti-adrenals such as aminoglutethimide, mitotane, trilostane, anti-androgens such as flutamide, nilutamide, bicalutamide, leuprolide, and goserelin; antibiotics such as aclacinomysins, actinomycin, authramycin, azasenne, bleomycins, cactinomycin, calicheamicin, carabicin, caminomycin, carzinophilm, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, etreptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); antimetabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, thethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids, or derivatives of any of the above may also be used.

Such a chemotherapeutic or other cytotoxic agent, as disclosed above, may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt eet al., (ed.): 247-267, Humana Press, 1985. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies of the present invention include but are not limited to any of the aforementioned chemotherapeutic agents.

In various other embodiments, the antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but are not limited to non-steroidal anti-inflammatory drugs (NSAIDs) such as aspirin, ibuprofen, celecoxib, diclofenac, etodolac, fenoprofen, indomethacin, ketoralac, oxaprozin, nabumentone, sulindac, tolmentin, rofecoxib, naproxen, ketoprofen, and nabumetone, steroids (e.g. glucocorticoids, dexamethasone, cortisone, hydroxycortisone, methylprednisolone, prednisone, prednisolone, trimcinolone, azulfidineicosanoids such as prostaglandins, thromboxanes, and leukotrienes, as well as topical steroids such as anthrahn, calcipotriene, clobetasol, and tazarotene), cytokines such as TGFβ, IFNα, IFNβ, IFNγ, IL-2, IL-4, IL-10, cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD402, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab), heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocriptine, cyclophosphamide, cyclosporine A, D-penicillamine, deoxyspergualm, FK506, glutaraldehyde, gold, hydroxychloroquine, leflunomide, malononitriloamides (e.g. leflunomide), methotrexate, minocycline, mizoribine, mycophenolate mofetil, rapamycin, and sulfasasazine.

In various embodiments, antibodies of the present invention are co-administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone, thyroxine; insulin; proinsulin, relaxin, prorelaxin, glycoprotein hormones such as follicle stimulating hormone (FSH), thyroid stimulating hormone (TSH), and luteinizing hormone (LH), hepatic growth factor, fibroblast growth factor; prolactin, placental lactogen, tumor necrosis factor-alpha and -beta; mullerian-inhibiting substance, mouse gonadotropin-associated peptide, inhibin; activin, vascular endothelial growth factor; integrin; thrombopoietin (TPO); nerve growth factors such as NGF-beta; platelet-growth factor, transforming growth factors (TGFs) such as TGF-alpha and TGF-beta, insulin-like growth factor-I and -II; erythropoietin (EPO), osteoinductive factors, interferons such as interferon-alpha, beta, and -gamma, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-1 alpha, IL-2, IL-3, IL-4, IL-5, IL-6, IL-7, IL-8, IL-9, IL-10, IL-11, IL-12, IL-15, a tumor necrosis factor such as TNF-alpha or TNF-beta, and other polypeptide factors including LIF and kit ligand (KL) As used herein, the term cytokine includes proteins from natural sources or from recombinant cell culture, and biologically active equivalents of the native sequence cytokines.

In various embodiments, the cytokines or other agents co-administered serve to stimulate cells of the immune system. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand J. Immunol. 57. 221-8), may be co-administered. Also, agents that stimulate neutrophils, including but not limited to G-CSF, GM-CSF, and the like may be administered Furthermore, agents that promote migration of such immunostimulatory cytokines may be used. Also additional agents including but not limited to interferon gamma, IL-3 and IL-7 may promote one or more effector functions.

Alternatively, cytokines or other agents that inhibit effector cell function may be co-administered with the antibody of the present invention Such a mode of treatment may limit unwanted effector function The antibodies of the present invention may be combined with other therapeutic regimens. For example, in one embodiment, the patient to be treated with an antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient.

It is of course contemplated that the antibodies of the invention may employ in combination with still other therapeutic techniques such as surgery or phototherapy.

The present invention is further illustrated by the following examples. However, it should be understood, that the invention is not limited to the exemplified embodiments.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Materials & Methods

Indirect ELISA: Purified cANGPTL4 was immobilized onto carboxylated polystyrene microwell plate (Biomat), using EDC(1-Ethyl-3-(3-dimethylaminopropyl)carbodiimide)-mediated amination at 37° C. for 2 h. Purified BSA was used as a control. The micro-well plates were washed three times with 300 µL/well with 1×PBST (PBS with 0.1% Tween 20). The wells were blocked with 2% BSA (300 µL/well) in PBS at 37° C. for 1 h. The micro-well plates were washed three times with 300 µL/well with 1×PBST. Serially diluted Antuzumabs (starting at 10 ug/mL) were added and incubated at 37° C. for 1 h. The micro-well plates were washed four times with 300 µL/well with 1×PBST. Next, 100 µL anti-human Fc IgG-HRP(1:2K dilution) in PBS was added and incubated for 1 h to detect bound humanized antibodies. The plate was washed five times with 300 µl/well 1×PBST. Finally, one-step TMB (3,3',5,5'-Tetramethylbenzidine) was added and incubated at room temperature for 30 min. The reaction was stopped by adding 100 µl of 2 M $H_{25}O_4$. The absorbance was measured at 450 nm.

Surface Plasmon Resonance (SPR): Sensor CM5 chips and amine coupling kits were from GE Healthcare. Purified cANGPTL4 was immobilized onto a CM5-carboxylated dextran sensor chip by amine coupling using the Surface Prep Module of BIACORE 3000 as recommended by the manufacturer (BIAcore). Antuzumab (0.16, 0.32, 0.63, 1.25, 2.50, and 5.0 µm) diluted and buffered with 50 mm Tris, pH 8.0, was introduced into the cANGPTL4-conjugated CM5 chip at a flow rate of 5 µl/min for 10 min with running buffer (50 mm Tris, pH 8.0, 100 mm NaCl). After incubation for 45 s, the chamber was washed with the same buffer, and the bound molecules were subsequently eluted using 10 mm glycine, pH 6.0. The CM5 chip was reused after washing with running buffer for 10 min at 20 µl/min. Each sensorgram was corrected by subtracting a sensorgram obtained from a reference flow cell with no immobilized protein. Global fitting of the SPR data was used to determine the association ($K_{ass}$) and dissociation ($K_{diss}$) with Scrubber 2 software. Values are given as the mean±S.D. of three independent preparations of Antuzumab.

3D culture of tumoroid spheroids with micropatterned agarose hydrogel: 1% Agarose (w/v in PBS) micro-molds were casted using MicroTissues® 3D Petri Dish® micro-mold. Each micro-mold has 256 small wells which yield 256-spheroids. The micro-mold was transferred to a 12-well plate and UV-irradiated for 45 minutes before used. 120 µL of $1.5×10^6$/mL of dispersed cancer cell suspension in DMEM were seeded onto each micro-mold. After 5-minutes of settling, 1.5 mL of media was added into each well and the cells were cultured for 20 hours prior to treatment. For treatment, 512 spheroids (in 2 micro-mold) were flushed out of the small wells using media and centrifuged at 200 g for 4 min before resuspended in 4.8 mL of DMEM. 400 µL of suspended spheroids was pipetted into agarose-coated 12-well plates for monoclonal antibody treatment.

Treatment with Antuzumab in normoxia and hypoxia: Tumoroid spheroids were treated for 16 hours in varying concentrations, 1-8 µg/mL of Antuzumab For negative control, 6 µg/mL of IgG was used. Hypoxia was induced by treating spheroids in hypoxic chamber at 1% 02 concentration (Stem Cell Technology, USA).

Cell viability test & establishing dose-response curve: Cancer tumoroids were collected from wells and trypsinized for 4 minutes in 300 µL of 0.05% trypsin. The dispersed cells were resuspended in 50 µL culture media. The ADAM-MC Automatic Cell Counter (NanoEnTek, Singapore) was used to determine cell viability. The ADAM-MC software measures the total cells and the non-viable cells and tabulates the cell viability. The half maximal inhibitory concentration ($IC_{50}$) is defined as the concentration of drug administered to 3D in-vitro cell model to elicit 50% death of total cells. $IC_{50}$ was calculated using Graphpad PRISM 7's built-in non-linear regression model and sigmoidal dose-response (variable slope) analysis.

Microscopy & immunofluorescence for imaging live/dead cells: 3D cell cultures were monitored and confirmed by JuLl Stage: Real-Time Cell History Recorder (NanoEnTek, Singapore). Imaging of immunofluorescence was conducted in parallel using Hoechst 33342 fluorescent dye and 1 µg/mL of PI (Thermofisher Scientific, USA) to stain cells for live and dead cells respectively.

Orthotopic bladder tumor xenografts. The protocol was as described by Huebner et al (An orthotopic xenograft model for high-risk non-muscle invasive bladder cancer in mice: influence of mouse strain, tumor cell count, dwell time and bladder pretreatment. BMC Cancer 17, 790 (2017).

Example 1

Starting from known murine monoclonal antibody mAb11F6C4, four humanized heavy chain variable regions (ANGH1-4) and light chain variable regions (ANGK1-4) were synthesized. Their DNA sequences and amino acid sequences are shown in FIG. 1 and also set forth in SEQ ID Nos. 7-14. A comparison of the amino acid sequences of ANGH1-4 and ANGK1-4 with the heavy and light chains amino acid sequence from the mouse-derived mAb11F6C4 is shown in FIG. 1. The shaded amino acid regions (dark letters) highlight the differences between the humanized and mouse-derived heavy and light chains. The CDR regions are shown as shaded boxes with white letters.

A combination of 16 pairs of ANGH+ANGK were transfected into CHO cells, of which 6 did not yield stable humanized monoclonal antibody cell lines. The table is indicated below.

TABLE 1

Humanized monoclonal antibodies against human cANGPTL4

| Heavy chain | Light chain variable region (V$_L$) | | | |
|---|---|---|---|---|
| variable region (V$_H$) | ANGK1 (SEQ ID NO: 8) | ANGK2 (SEQ ID NO: 10) | ANGK3 (SEQ ID NO: 12) | ANGK4 (SEQ ID NO: 14) |
| ANGH1 (SEQ ID NO: 7) | ANG27 (Antuzumab 3) | ANG28 | ANG29 | X |
| ANGH2 (SEQ ID NO: 9) | ANG37 | ANG38 | ANG39 | X |
| ANGH3 (SEQ ID NO: 11) | ANG47 | ANG48 | ANG49 (Antuzumab 1) | X |
| ANGH4 (SEQ ID NO: 13) | X | X | X | ANG50 (Antuzumab 2) |

X denotes unstable monoclonal antibody cell lines.

Example 2

Indirect ELISA and surface plasmon resonance (SPR) of the stable antibodies of Example 1 identified 3 humanized mAb with 7×, 5× and 2× higher affinity for the antigen compared with the original mouse-derived mAb (11F6C4; V$_H$: SEQ ID NO: 23; V$_L$: SEQ ID NO:24)) against human cANGPTL4 antigen. The results of the ELISA assays are shown in FIG. 2. The results of the SPR assays are shown in Table 2 below. These 3 humanized mAb with higher affinity (termed Antuzumab 1, 2 and 3) were selected for stable cell line production.

TABLE 2

| | Kass (M−1 s−1) | Kdiss (s−1) | KD (nM) | STDEV | Fold increase |
|---|---|---|---|---|---|
| Antuzumab 1 | 6.576 E+05 | 6.934 E−04 | 1.054 | 0.062 | 7.86 |
| Antuzumab 2 | 4.954 E+05 | 7.641 E−04 | 1.542 | 0.045 | 5.37 |
| Antuzumab 3 | 2.122 E+05 | 9.484 E−04 | 4.470 | 0.075 | 1.85 |
| Control 11F6C4 | 1.093 E+05 | 9.052 E−04 | 8.284 | 0.151 | 1.00 |

Example 3

Anti-tumor assays using in vitro 3D tumoroid models for bladder cancer (T24, UMUC3), gastric cancer (MKN74) and glioblastoma (U87) were performed for the three higher affinity humanized antibodies and the murine antibody as reference. The 1050 values (μg/mL) are shown in Table 3 below.

TABLE 3

| | T24 | UMUC3 | MKN74 | U87 |
|---|---|---|---|---|
| Antuzumab 1 | 0.273 | 0.399 | 0.622 | 2.318 |
| Antuzumab 2 | 0.414 | 1.075 | 0.631 | 4.255 |
| Antuzumab 3 | 3.336 | 1.086 | 3.272 | 8.556 |
| 11F6C4 | 2.675 | 2.815 | 3.124 | 9.910 |

Example 4

Growth and maintenance of hybridomas of Antuzumab 1, 2 and 3 was determined over 2 batches of production. The results are shown in Table 4.

TABLE 4

| | Batch 1 | | Batch 2 | |
|---|---|---|---|---|
| | Cell density | mAU (OD) | Cell density | mAU (OD) |
| Antuzumab 1 | 4.67 × 10$^5$/ml | 650 | 2.4 × 10$^5$/ml | 825 |
| Antuzumab 2 | 7.72 × 10$^5$/ml | 775 | 2.03 × 10$^5$/ml | 1200 |
| Antuzumab 3 | 1.38 × 10$^6$/ml | 750 | 1.07 × 10$^6$/ml | 1050 |

Example 5

ANGPTL4 erodes cell-cell integrity causing vasculature leakage in the retina, which is an early phenomenon in diabetic retinopathy and age-macular degeneration. Antuzumab 1 was able to block the action of ANGPTL4 and prevent vasculature leakage in retina.

Secretion of ANGPTL4 from MIO-M1 after hypoxia treatment. (verified with Western blot). Control medium was Normoxia medium from MIO-M1 cells after 48 h. Treatment medium was Hypoxia medium from MIO-M1 cells after 48 h. Measurements taken at 6, 24 and 48 h.

High levels of ANGPTL4 were secreted by MIO-M1 (Muller cells) cells under hypoxic conditions, which reduced in transendothelial impedance at 6 h (1st time point of measurement). At 24-48 h, the transendothelial impedance has reached saturation (FIG. 3A). Next, 10 ng of Antuzumab 1 were added to conditioned medium from hypoxia-treated MIO-M1 cells. Antuzumab 1 was able to inhibit vascular leakiness caused by conditioned medium of hypoxia induced MIO-M1 (FIG. 3B).

Example 6

Figure 4:
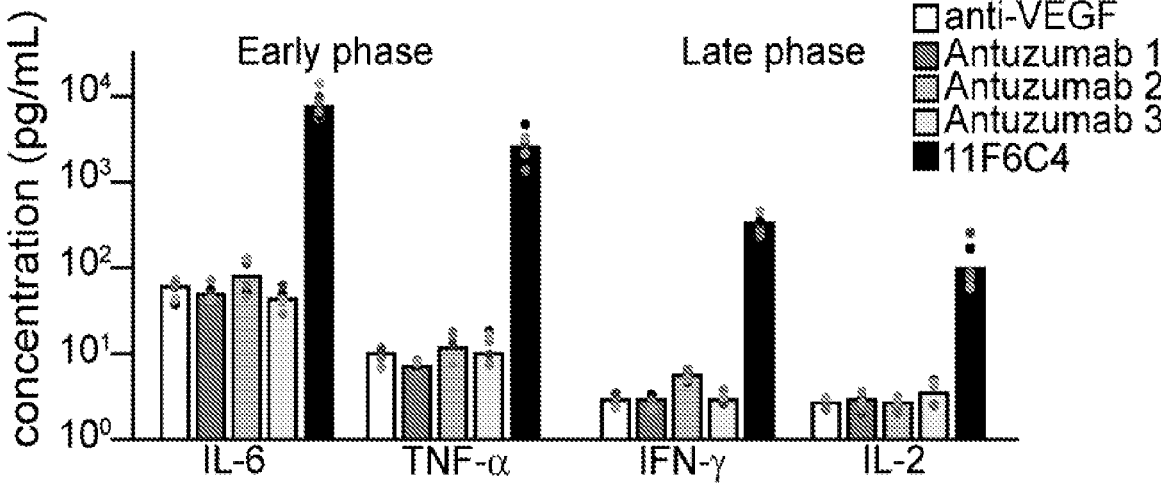
FIG. 4 shows the results of abridged in vitro comparative immunogenicity assessment (IVCIA) for antibodies Antuzumab 1, 2 and 3.

Antuzumab 1, 2 and 3 showed reduced immunogenicity in early and late responses when compared with original mAB 11F6C4 as determined by abridged in vitro comparative immunogenicity assessment (IVCIA). The results are shown in FIG. 4.

Example 7

Figure 5:
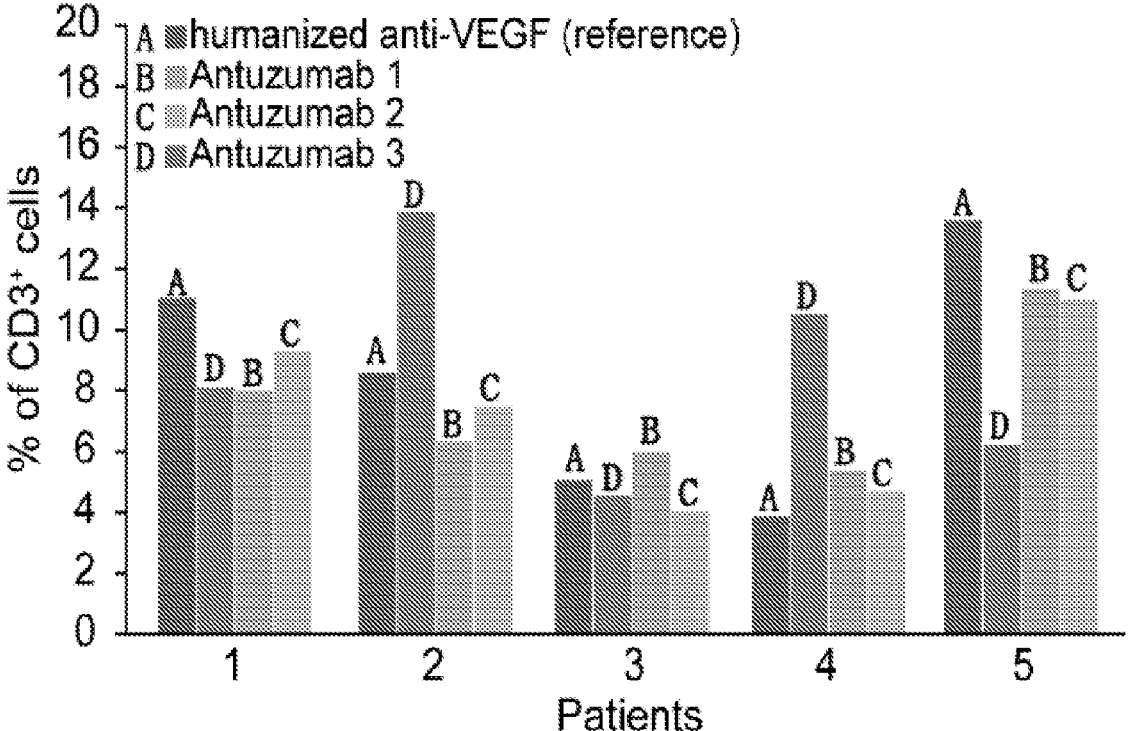
FIG. 5 shows the results of an in vitro assay that can elicit antigen specific effector T cell responses as percentage of total T cells induced by anti-VEGF, Antuzumab 1, 2 and 3.

An immune response to a biotherapeutic can be induced when the therapeutic is processed and presented by antigen presenting cell to T helper cells. The percentage of total T cells induced by anti-VEGF, Antuzumab 1, 2 and 3 was evaluated using an in vitro assay that can elicit antigen specific effector T cell responses. The results are shown in FIG. 5.

Antuzumab 1 and 2 showed comparable immunogenicity as humanized anti-VEGF (bevacizumab), as indicated by percentage of T cell population from five human PBMC. Antuzumab 3 had a higher percentage of T cells for patient 2 and 4 when compared to bevacizumab. However, Antuzumab 3 was comparable to published data on adalimumab, infliximab (anti-TNFalpha) and rituximab (anti-CD20).

Example 8

Figure 6:
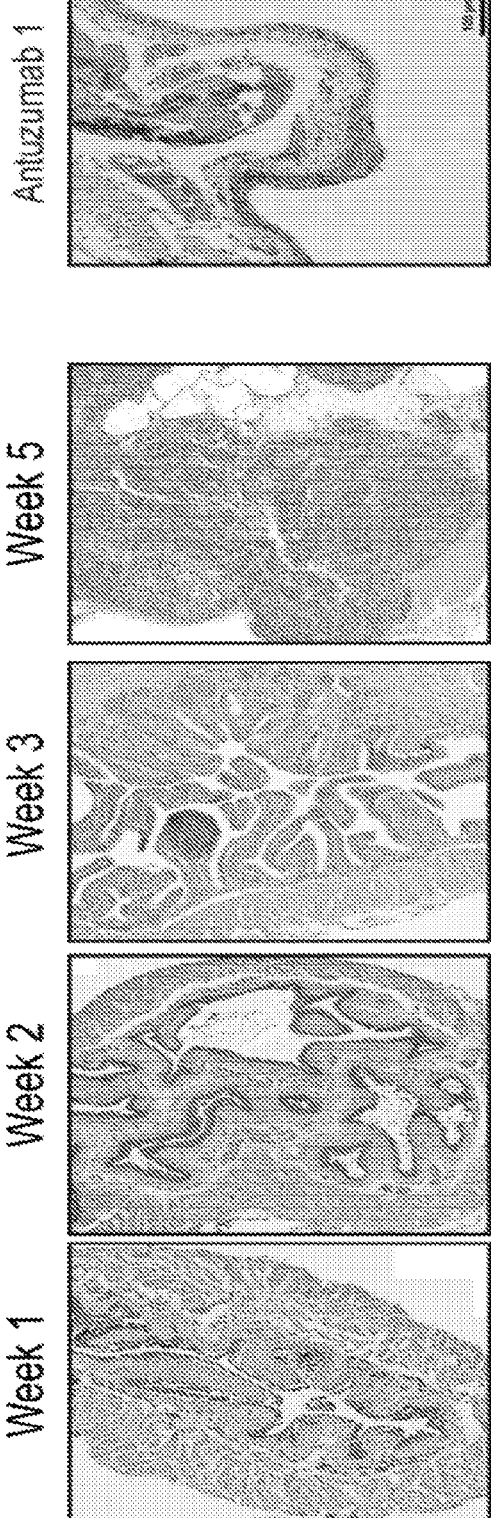
FIG. 6 shows microscopy images of histologic samples of an orthotopic bladder tumor xenograft model for high-risk NMIBC in an animal model (immunocompromised NSG mice) using human UMUC3 cells with and without Antuzumab1 (10 µg/mL) administrated intravesically at week 3 post instillation of cancer cells.

An orthotopic bladder tumor xenograft model for high-risk NMIBC was developed in an animal model (immuno-compromised NSG mice) using human UMUC3 cells. At Antuzumab1 (10 µg/mL) attenuated growth of bladder tumor when administrated intravesically at week 3 post instillation of cancer cells attenuated the growth. The results are shown in FIG. 6. This experiment showed the effectiveness of Antuzumab 1 in bladder cancer treatment through the inhibition of cANGPTL4.

The invention claimed is:

1. A humanized antibody directed against the C-terminal region of angiopoietin-like 4 protein (cANGPTL4), said humanized antibody comprising a heavy chain variable domain and a light chain variable domain with human framework regions, the heavy chain variable domain comprising murine $V_H$ CDR1, $V_H$ CDR2, and $V_H$ CDR3 regions having the amino acid sequences set forth in SEQ ID Nos. 1-3, and the light chain variable domain comprising murine $V_L$ CDR1, $V_L$ CDR2, and $V_L$ CDR3 regions having the amino acid sequence set forth in SEQ ID Nos. 4-6, wherein:

(1) the heavy chain variable domain comprises of the amino acid sequence set forth in SEQ ID NO:11 (ANGH3) or a variant thereof and the light chain variable domain comprises of the amino acid sequence set forth in SEQ ID NO: 12 (ANGK3) or a variant thereof; or (2) the heavy chain variable domain comprises of the amino acid sequence set forth in SEQ ID NO:7 (ANGH1) or a variant thereof and the light chain variable domain comprises of the amino acid sequence set forth in any one of SEQ ID Nos: 8 (ANGK1), 10 (ANGK2), or 12 (ANGK3) or a variant thereof;

(3) the heavy chain variable domain comprises of the amino acid sequence set forth in SEQ ID NO:9 (ANGH2) or a variant thereof and the light chain variable domain comprises of the amino acid sequence set forth in any one of SEQ ID Nos: 8 (ANGK1), 10 (ANGK2), or 12 (ANGK3) or a variant thereof;

(4) the heavy chain variable domain comprises of the amino acid sequence set forth in SEQ ID NO:11

(ANGH3) or a variant thereof and the light chain variable domain comprises of the amino acid sequence set forth in any one of SEQ ID Nos: 8 (ANGK1) or 10 (ANGK2) or a variant thereof, or (5) the heavy chain variable domain comprises of the amino acid sequence set forth in SEQ ID NO:13 (ANGH4) or a variant thereof and the light chain variable domain comprises of the amino acid sequence set forth in SEQ ID NO:14 or a variant thereof; wherein the variants are invariable with respect to the CDR regions as defined in SEQ ID Nos. 1-6 and share at least 80% sequence identity with the respective reference sequence.

2. The antibody of claim 1, wherein (1) the heavy chain variable domain comprises of the amino acid sequence set forth in SEQ ID NO:7 (ANGH1) or a variant thereof and the light chain variable domain comprises of the amino acid sequence set forth in any one of SEQ ID Nos: 8 (ANGK1), 10 (ANGK2), or 12 (ANGK3) or a variant thereof;

(2) the heavy chain variable domain comprises of the amino acid sequence set forth in SEQ ID NO:9 (ANGH2) or a variant thereof and the light chain variable domain comprises of the amino acid sequence set forth in any one of SEQ ID Nos: 8 (ANGK1) or 12 (ANGK3) or a variant thereof;

(3) the heavy chain variable domain comprises of the amino acid sequence set forth in SEQ ID NO:11 (ANGH3) or a variant thereof and the light chain variable domain comprises of the amino acid sequence set forth in any one of SEQ ID Nos: 10 (ANGK2) or 12 (ANGK3) or a variant thereof; or (4) the heavy chain variable domain comprises of the amino acid sequence set forth in SEQ ID NO:13 (ANGH4) or a variant thereof and the light chain variable domain comprises of the amino acid sequence set forth in SEQ ID NO:14 or a variant thereof.

3. The antibody of claim 1, wherein (1) the heavy chain variable domain comprises of the amino acid sequence set forth in SEQ ID NO:7 or a variant thereof and the light chain variable domain comprises of the amino acid sequence set forth in SEQ ID NO:8 or a variant thereof; or (2) the heavy chain variable domain comprises of the amino acid sequence set forth in SEQ ID NO: 11 or a variant thereof and the light chain variable domain comprises of the amino acid sequence set forth in SEQ ID NO: 12 or a variant thereof; or (3) the heavy chain variable domain comprises of the amino acid sequence set forth in SEQ ID NO: 13 or a variant thereof and the light chain variable domain comprises of the amino acid sequence set forth in SEQ ID NO:14 or a variant thereof.

4. The antibody of claim 1, wherein the heavy chain variable domain comprises of the amino acid sequence set forth in SEQ ID NO:11 or a variant thereof and the light chain variable domain comprises of the amino acid sequence set forth in SEQ ID NO:12 or a variant thereof.

5. The antibody of claim 1, wherein the antibody is an IgG immunoglobulin, preferably an IgG1 immunoglobulin, more preferably an IgG1 kappa immunoglobulin.

6. The antibody of claim 1, wherein the antibody comprises a human IgG1 constant region within a heavy chain of the immunoglobulin and a human constant region within a light chain of the immunoglobulin.

7. A method of treating a patient suffering from a c-ANGPTL4-expressing cancer or tumour, the method comprising administering a therapeutically effective amount of the antibody according to claim 1 to said patient.

8. A nucleic acid molecule comprising a nucleotide sequence encoding a heavy and/or light chain variable domain of the antibody of claim 1.

9. The nucleic acid molecule of claim 8, wherein the nucleic acid molecule comprises a nucleotide sequence encoding the variable domain of the heavy chain as set forth in any one of SEQ ID Nos: 15, 17, 19, and 21.

10. The nucleic acid molecule of claim 8, wherein the nucleic acid molecule comprises a nucleotide sequence encoding the variable domain of the light chain as set forth in any one of SEQ ID Nos: 16, 18, 20, and 22.

11. The nucleic acid molecule of claim 8, wherein the nucleic acid molecule is a vector, preferably a plasmid.

* * * * *

```
                          SEQUENCE LISTING

<160> NUMBER OF SEQ ID NOS: 24

<210> SEQ ID NO 1
<211> LENGTH: 7
<212> TYPE: PRT
<213> ORGANISM: Artificial
<220> FEATURE:
<223> OTHER INFORMATION: VH CDR1

<400> SEQUENCE: 1

Thr Ser Gly Met Gly Val Gly
1               5

<210> SEQ ID NO 2
<211> LENGTH: 16
<212> TYPE: PRT
<213> ORGANISM: Artificial
<220> FEATURE:
<223> OTHER INFORMATION: VH CDR2

<400> SEQUENCE: 2

His Ile Trp Trp Asp Asp Asp Lys Tyr Tyr Asn Pro Ser Leu Lys Ser
1               5                   10                  15

<210> SEQ ID NO 3
<211> LENGTH: 9
<212> TYPE: PRT
<213> ORGANISM: Artificial
<220> FEATURE:
<223> OTHER INFORMATION: VH CDR3

<400> SEQUENCE: 3

Lys Asp Tyr Gly Ser Ser Tyr Asp Tyr
1               5

<210> SEQ ID NO 4
<211> LENGTH: 15
<212> TYPE: PRT
<213> ORGANISM: Artificial
<220> FEATURE:
<223> OTHER INFORMATION: VL CDR1

<400> SEQUENCE: 4

Lys Ala Ser Gln Ser Val Asp Tyr Asp Gly Asp Ser Tyr Leu Asn
1               5                   10                  15

<210> SEQ ID NO 5
<211> LENGTH: 7
<212> TYPE: PRT
<213> ORGANISM: Artificial
<220> FEATURE:
<223> OTHER INFORMATION: VL CDR2

<400> SEQUENCE: 5

Thr Ala Ser Asn Leu Glu Ser
1               5

<210> SEQ ID NO 6
<211> LENGTH: 8
<212> TYPE: PRT
```

```
<213> ORGANISM: Artificial
<220> FEATURE:
<223> OTHER INFORMATION: VL CDR3
<220> FEATURE:
<221> NAME/KEY: MISC_FEATURE
<222> LOCATION: (1)..(1)
<223> OTHER INFORMATION: Xaa can be Phe (F) or Gln (Q)

<400> SEQUENCE: 6

Xaa Gln Ser Asn Glu Asp Pro Trp
1               5

<210> SEQ ID NO 7
<211> LENGTH: 119
<212> TYPE: PRT
<213> ORGANISM: Artificial
<220> FEATURE:
<223> OTHER INFORMATION: VH domain ANGH1

<400> SEQUENCE: 7

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Asp Tyr Gly Ser Ser Tyr Asp Tyr Trp Gly Gln Gly
            100                 105                 110

Thr Leu Val Thr Val Ser Ser
        115

<210> SEQ ID NO 8
<211> LENGTH: 111
<212> TYPE: PRT
<213> ORGANISM: Artificial
<220> FEATURE:
<223> OTHER INFORMATION: VL domain ANGK1

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
            35                  40                  45

Lys Leu Leu Ile Tyr Thr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Trp Thr Phe Gly Gln Gly Thr Lys Val Glu Ile Lys
            100                 105                 110
```

-continued

```
<210> SEQ ID NO 9
<211> LENGTH: 119
<212> TYPE: PRT
<213> ORGANISM: Artificial
<220> FEATURE:
<223> OTHER INFORMATION: VH domain ANGH2

<400> SEQUENCE: 9

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Lys Asp Tyr Gly Ser Ser Tyr Asp Tyr Trp Gly Gln Gly
            100                 105                 110

Thr Leu Val Thr Val Ser Ser
        115

<210> SEQ ID NO 10
<211> LENGTH: 111
<212> TYPE: PRT
<213> ORGANISM: Artificial
<220> FEATURE:
<223> OTHER INFORMATION: VL domain ANGK2

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser Tyr Leu Asn Trp Tyr Gln Gln Lys Pro Gly Gln Ala Pro
        35                  40                  45

Arg Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gln Gly Thr Lys Leu Glu Ile Lys
            100                 105                 110

<210> SEQ ID NO 11
<211> LENGTH: 119
<212> TYPE: PRT
<213> ORGANISM: Artificial
<220> FEATURE:
<223> OTHER INFORMATION: VH domain ANGH3

<400> SEQUENCE: 11

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30
```

```
Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Asp Tyr Gly Ser Ser Tyr Asp Tyr Trp Gly Gln Gly
            100                 105                 110

Thr Thr Val Thr Val Ser Ser
        115

<210> SEQ ID NO 12
<211> LENGTH: 111
<212> TYPE: PRT
<213> ORGANISM: Artificial
<220> FEATURE:
<223> OTHER INFORMATION: VL domain ANGK3

<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Ser Val Asp Tyr Asp
            20                  25                  30

Gly Asp Ser Tyr Leu Asn Trp Tyr Leu Gln Lys Pro Gly Gln Ser Pro
        35                  40                  45

Arg Leu Leu Ile Tyr Thr Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Phe Gln Ser Asn
                85                  90                  95

Glu Asp Pro Trp Thr Phe Gly Gln Gly Thr Lys Leu Glu Ile Lys
            100                 105                 110

<210> SEQ ID NO 13
<211> LENGTH: 119
<212> TYPE: PRT
<213> ORGANISM: Artificial
<220> FEATURE:
<223> OTHER INFORMATION: VH domain ANGH4

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Asp Leu Thr Met Thr Phe Met Asp Pro Trp Asp Thr Ala Thr Tyr Tyr
                85                  90                  95

Cys Ala His Lys Asp Tyr Gly Ser Ser Tyr Asp Tyr Trp Gly Gln Gly
```

-continued

```
                 100             105             110

Thr Leu Val Thr Val Ser Ser
      115

<210> SEQ ID NO 14
<211> LENGTH: 111
<212> TYPE: PRT
<213> ORGANISM: Artificial
<220> FEATURE:
<223> OTHER INFORMATION: VL domain ANGK4

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Leu Asn Trp Tyr Gln Gln Lys Pro Gly Lys Ala Pro
        35                  40                  45

Asn Leu Leu Ile Tyr Thr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Trp Thr Phe Gly Glu Gly Thr Lys Val Glu Ile Lys
            100                 105                 110

<210> SEQ ID NO 15
<211> LENGTH: 357
<212> TYPE: DNA
<213> ORGANISM: Artificial
<220> FEATURE:
<223> OTHER INFORMATION: VH domain ANGH1

<400> SEQUENCE: 15
caaattactc tgaaggagag cgggcccacc ctggtgaagc ccacccagac cctgaccctg     60
acctgtacct tcagcgggtt cagcctgagc accagcggga tgggggtggg gtggatcaga    120 cagcccccg ggaaggccct ggagtggctg cccacatct ggtgggatga tgataagtac     180
tacaacccca gcctgaagag cagactgacc atcaccaagg ataccagcaa gaaccaggtg    240
gtgctgacca tgaccaacat ggatcccgtg ataccgcca cctactactg tgccagaaag     300
gattacggga gcagctacga ttactggggg cagggggactc ttgttaccgt ttctagc      357

<210> SEQ ID NO 16
<211> LENGTH: 333
<212> TYPE: DNA
<213> ORGANISM: Artificial
<220> FEATURE:
<223> OTHER INFORMATION: VL domain ANGK1

<400> SEQUENCE: 16
gatatcgtga tgacccagag ccccgatagc ctggccgtga gcctggggga gagagccacc     60
atcaactgta aggccagcca gagcgtggat tacgatgggg atagctacct gaactggtac    120
cagcagaagc ccgggcagcc ccccaagctg ctgatctaca ccgccagcaa cctggagagc    180
ggggtgcccg atagattcag cgggagcggg agcgggaccg atttcaccct gaccatcagc    240
agcctgcagg ccgaggatgt ggccgtgtac tactgtcagc agagcaacga ggatccctgg    300
accttcgggc aggggactaa ggttgagatt aaa                                 333
```

-continued

```
<210> SEQ ID NO 17
<211> LENGTH: 357
<212> TYPE: DNA
<213> ORGANISM: Artificial
<220> FEATURE:
<223> OTHER INFORMATION: VH domain ANGH2

<400> SEQUENCE: 17
caagtgaccc tgaaggagag cgggcccgtg ctggtgaagc ccaccgagac cctgaccctg      60
acctgtaccg tgagcgggtt cagcctgagc accagcggga tggggtgggg gtggatcaga     120 cagcccccccg ggaaggccct ggagtggctg cccacatct ggtgggatga tgataagtac     180 tacaaccoca gcctgaagag cagactgacc atcagcaagg ataccagcaa gagccaggtg     240
gtgctgacca tgaccaacat ggatcccgtg ataccgcca cctactactg tgccagaaag      300
gattacggga gcagctacga ttactggggg caggggactc ttgttaccgt ttctagc        357

<210> SEQ ID NO 18
<211> LENGTH: 333
<212> TYPE: DNA
<213> ORGANISM: Artificial
<220> FEATURE:
<223> OTHER INFORMATION: VL domain ANGK2

<400> SEQUENCE: 18
gagatcgtgc tgacccagag ccccgccacc ctgagcctga gccccgggga gagagccacc      60
ctgagctgta aggccagcca gagcgtggat tacgatgggg atagctacct gaactggtac     120
cagcagaagc ccgggcaggc ccccagactg ctgatctaca ccgccagcaa cctggagagc     180
gggatccccg ccagattcag cgggagcggg agcgggaccg atttcacccct gaccatcagc     240 agcctggagc ccgaggattt cgccgtgtac tactgtcagc agagcaacga ggatccctgg      300
accttcgggc aggggactaa gcttgagctt aaa                                   333

<210> SEQ ID NO 19
<211> LENGTH: 357
<212> TYPE: DNA
<213> ORGANISM: Artificial
<220> FEATURE:
<223> OTHER INFORMATION: VH domain ANGH3

<400> SEQUENCE: 19
caggtgaccc tgaaggagag cgggcccacc ctggtgaagc ccacccagac cctgaccctg      60
acctgtacct tcagcgggtt cagcctgagc accagcggga tggggtgggg gtggatcaga     120 cagcccccccg ggaaggccct ggagtggctg cccacatct ggtgggatga tgataagtac     180 tacaaccoca gcctgaagag cagactgacc atcagcaagg ataccagcaa gaaccaggtg     240
gtgctgacca tgaccaacat ggatcccgtg ataccgcca cctactactg tgccagaaag      300
gattacggga gcagctacga ttactggggg cagggggacga cggtcaccgt ctcctca        357

<210> SEQ ID NO 20
<211> LENGTH: 333
<212> TYPE: DNA
<213> ORGANISM: Artificial
<220> FEATURE:
<223> OTHER INFORMATION: VL domain ANGK3

<400> SEQUENCE: 20
gatatcgtga tgacccagag cccccctgagc ctgcccgtga cccccggggga gcccgccagc     60
```

-continued

```
atcagctgta aggccagcca gagcgtggat tacgatgggg atagctacct gaactggtac      120
ctgcagaagc ccgggcagag ccccagactg ctgatctaca ccgccagcaa cctggagagc      180
ggggtgcccg atagattcag cgggagcggg agcgggaccg atttcaccct gaagatcagc      240
agagtggagg ccgaggatgt gggggtgtac tactgtttcc agagcaacga ggatccctgg      300
accttcgggc aggggactaa gcttgagctt aaa                                  333
```

```
<210> SEQ ID NO 21
<211> LENGTH: 357
<212> TYPE: DNA
<213> ORGANISM: Artificial
<220> FEATURE:
<223> OTHER INFORMATION: VH domain ANGH4

<400> SEQUENCE: 21
```

```
cagatcaccc tgaaggagag cgggcccacc ctggtgaagc ccacccagac cctgaccctg       60
acctgtacct tcagcgggtt cagcctgagc accagcggga tggggtgggg gtggatcaga      120 cagcccccg ggaaggccct ggagtggctg cccacatct ggtgggatga tgataagtac       180
tacaacccca gcctgaagag cagactgacc atcaccaagg ataccagcaa gaaccaggtg      240
gatctgacca tgaccttcat ggatccctgg ataccgcca cctactactg tgcccacaag       300
gattacggga gcagctacga ttactggggg caggggactc ttgttaccgt ttctagc        357
```

```
<210> SEQ ID NO 22
<211> LENGTH: 333
<212> TYPE: DNA
<213> ORGANISM: Artificial
<220> FEATURE:
<223> OTHER INFORMATION: VL domain ANGK4

<400> SEQUENCE: 22
```

```
gatatccaga tgacccagag ccccagcagc ctgagcgcca gcgtgggga tagagtgacc        60 atcacctgta aggccagcca gagcgtggat tacgatgggg atagctacct gaactggtac      120
cagcagaagc ccgggaaggc ccccaacctg ctgatctaca ccgccagcaa cctggagagc      180
ggggtgccca gcagattcag cgggagcggg agcgggaccg atttcaccct gaccatcagc      240
agcctgcagc ccgaggattt cgccacctac tactgtcagc agagcaacga ggatccctgg      300
accttcgggg aggggactaa ggttgagatt aaa                                  333
```

```
<210> SEQ ID NO 23
<211> LENGTH: 119
<212> TYPE: PRT
<213> ORGANISM: Artificial
<220> FEATURE:
<223> OTHER INFORMATION: murine mAb11F6C4 heavy chain variable domain

<400> SEQUENCE: 23
```

```
Gln Ile Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80
```

-continued

```
Phe Leu Lys Ile Thr Ser Val Asp Thr Ala Asp Thr Ala Thr Tyr Tyr
                85                  90                  95

Cys Ala Arg Lys Asp Tyr Gly Ser Ser Tyr Asp Tyr Trp Gly Gln Gly
            100                105                110

Thr Thr Leu Thr Val Ser Ser
        115

<210> SEQ ID NO 24
<211> LENGTH: 111
<212> TYPE: PRT
<213> ORGANISM: Artificial
<220> FEATURE:
<223> OTHER INFORMATION: murine mAB11F6C4 light chain variable domain

<400> SEQUENCE: 24

Asp Ile Val Leu Thr Gln Ser Pro Ala Ser Leu Ala Val Ser Leu Gly
1               5                  10                  15

Gln Arg Ala Thr Ile Ser Cys Lys Ala Ser Gln Ser Val Asp Tyr Asp
            20                  25                  30

Gly Asp Ser Tyr Leu Asn Trp Phe Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Thr Leu Glu Ile Lys
            100                105                110
```